(12) United States Patent
Hochman

(10) Patent No.: US 6,671,540 B1
(45) Date of Patent: Dec. 30, 2003

(54) METHODS AND SYSTEMS FOR DETECTING ABNORMAL TISSUE USING SPECTROSCOPIC TECHNIQUES

(76) Inventor: Daryl W. Hochman, 337 NE. 56th, Seattle, WA (US) 98105

( * ) Notice: Subject to any disclaimer, the term of this patent is extended or adjusted under 35 U.S.C. 154(b) by 0 days.

(21) Appl. No.: 09/366,500

(22) Filed: Aug. 3, 1999

Related U.S. Application Data

(63) Continuation-in-part of application No. 08/993,733, filed on Dec. 18, 1997, now Pat. No. 6,241,672, which is a continuation of application No. 08/477,468, filed on Jun. 7, 1995, now Pat. No. 5,699,798, which is a continuation-in-part of application No. 08/073,353, filed on Jun. 7, 1993, now Pat. No. 5,465,718, which is a continuation-in-part of application No. 07/894,270, filed on Jun. 8, 1992, now Pat. No. 5,438,989, which is a continuation-in-part of application No. 07/565,454, filed on Aug. 10, 1990, now Pat. No. 5,215,095.

(51) Int. Cl.$^7$ ................................................. A61B 5/05
(52) U.S. Cl. ........................................ 600/431; 600/477
(58) Field of Search ................................... 600/431, 476, 600/477, 478, 407; 348/68, 77; 382/128

(56) References Cited

U.S. PATENT DOCUMENTS

| | | | |
|---|---|---|---|
| 4,223,680 A | 9/1980 | Jöbsis | 128/633 |
| 4,417,591 A | 11/1983 | Culver | 128/731 |
| 4,450,478 A * | 5/1984 | Ledley | 358/111 |
| 4,472,732 A | 9/1984 | Bennett et al. | 358/22 |
| 4,515,165 A * | 5/1985 | Carroll | 128/664 |
| 4,541,438 A * | 9/1985 | Parker et al. | |
| 4,543,604 A | 9/1985 | Grosse | 358/111 |
| 4,556,057 A * | 12/1985 | Hiruma et al. | |
| 4,592,361 A * | 6/1986 | Parker et al. | 128/663 |
| 4,618,991 A | 10/1986 | Tabata et al. | 382/46 |
| 4,638,798 A | 1/1987 | Shelden et al. | 128/303 |
| 4,649,482 A | 3/1987 | Raviv et al. | 364/417 |
| 4,693,255 A * | 9/1987 | Beall | |
| 4,759,076 A | 7/1988 | Tanaka et al. | 382/46 |
| 4,767,717 A * | 8/1988 | Baisden | 128/653.1 |
| 4,768,513 A * | 9/1988 | Suzuki | |
| 4,773,097 A | 9/1988 | Suzaki et al. | 382/6 |
| 4,777,598 A | 10/1988 | Kellar et al. | 364/413.22 |
| 4,786,165 A | 11/1988 | Yamamoto et al. | 356/23 |
| 4,811,414 A | 3/1989 | Fishbine et al. | 382/52 |
| 4,835,532 A | 5/1989 | Fant | 340/728 |
| 4,852,579 A * | 8/1989 | Gilstad et al. | 128/665 |

(List continued on next page.)

FOREIGN PATENT DOCUMENTS

| | | | |
|---|---|---|---|
| EP | 0364966 | 4/1990 | A61B/6/00 |
| RU | 1026769 | 7/1983 | A61B/6/00 |
| WO | 8300970 | 3/1983 | H04N/5/32 |

OTHER PUBLICATIONS

Shinohara, Yukito, et al. "Towards near–infrared imaging of the brain," vol. 9, pp. 85–89.

Kinsey, J..H., et al. "Endoscopic System For Simultaneous Visual Examination And Electronic Detection Of Fluorescence," Rev. Sci. Instrum., vol. 51, No. 10, pp. 1403–1406 (Oct. 1980).

(List continued on next page.)

Primary Examiner—Shawna J. Shaw
(74) Attorney, Agent, or Firm—Ann W. Speckman; Lisa N. Benado

(57) ABSTRACT

The present invention provides methods and systems for determining the presence and location of abnormal or pathological tissue, for identifying and mapping the margins of abnormal tissue, such as tumor tissue during surgical or diagnostic procedures, and for grading and characterizing tumor tissue by detecting changes in the optical properties of spatially defined areas of an area of interest following administration of a contrast enhancing agent.

56 Claims, 15 Drawing Sheets

(9 of 15 Drawing Sheet(s) Filed in Color)

U.S. PATENT DOCUMENTS

| | | | |
|---|---|---|---|
| 4,869,247 A | | 9/1989 | Howard, III et al. ..... 128/303.1 |
| 4,930,516 A | | 6/1990 | Alfano et al. ............... 128/665 |
| 4,947,850 A | * | 8/1990 | Vanderkooi et al. |
| 4,972,331 A | | 11/1990 | Chance ....................... 364/550 |
| 4,999,614 A | * | 3/1991 | Ueda et al. .................. 358/113 |
| 5,014,709 A | * | 5/1991 | Bjelkhagen et al. ........ 128/665 |
| 5,027,817 A | * | 7/1991 | John ........................... 128/654 |
| 5,036,853 A | * | 8/1991 | Jeffcoat et al. |
| 5,042,494 A | * | 8/1991 | Alfano |
| 5,062,428 A | | 11/1991 | Chance ....................... 128/664 |
| 5,074,306 A | * | 12/1991 | Green et al. |
| 5,078,150 A | * | 1/1992 | Hara et al. ................... 600/476 |
| 5,079,698 A | * | 1/1992 | Grenier et al. ......... 364/413.13 |
| 5,094,837 A | * | 3/1992 | Bis ............................... 424/9 |
| 5,119,815 A | * | 6/1992 | Chance ....................... 128/665 |
| 5,185,809 A | * | 2/1993 | Kennedy et al. ......... 128/653.1 |
| 5,187,672 A | | 2/1993 | Chance et al. .............. 364/550 |
| 5,198,977 A | | 3/1993 | Salb ....................... 364/413.01 |
| 5,200,345 A | * | 4/1993 | Young ..................... 125/653.1 |
| 5,201,318 A | * | 4/1993 | Rava et al. |
| 5,205,291 A | * | 4/1993 | Potter |
| 5,211,938 A | * | 5/1993 | Kennedy et al. ............. 424/9.6 |
| 5,213,105 A | * | 5/1993 | Gratton et al. .............. 128/665 |
| 5,215,095 A | * | 6/1993 | Macvicar et al. |
| 5,239,998 A | * | 8/1993 | Krauthamer |
| 5,261,410 A | | 11/1993 | Alfano et al. ............... 128/664 |
| 5,284,154 A | * | 2/1994 | Raymond et al. ........... 128/741 |
| 5,318,024 A | | 6/1994 | Kittrell et al. ............... 128/634 |
| 5,353,799 A | | 10/1994 | Chance ....................... 128/664 |
| 5,363,854 A | * | 11/1994 | Martens et al. |
| 5,377,676 A | * | 1/1995 | Vari et al. |
| 5,386,827 A | | 2/1995 | Chance et al. .............. 128/633 |
| 5,438,989 A | * | 8/1995 | Hochman et al. |
| 5,465,718 A | * | 11/1995 | Hochman et al. |
| 5,553,614 A | | 9/1996 | Chance ....................... 128/633 |
| 5,555,885 A | | 9/1996 | Chance ....................... 128/654 |
| 5,564,417 A | | 10/1996 | Chance ....................... 128/633 |
| 5,660,181 A | | 8/1997 | Ho et al. ..................... 128/665 |
| 5,664,574 A | | 9/1997 | Chance ....................... 128/664 |
| 5,673,701 A | | 10/1997 | Chance ....................... 128/664 |
| 5,699,798 A | * | 12/1997 | Hochman et al. |
| 5,769,792 A | * | 6/1998 | Palcic et al. |
| 5,779,631 A | | 7/1998 | Chance ....................... 600/328 |
| 5,782,755 A | | 7/1998 | Chance et al. .............. 600/322 |
| 5,803,909 A | | 9/1998 | Maki et al. .................. 600/310 |
| 5,807,263 A | | 9/1998 | Chance ....................... 600/476 |
| 5,820,558 A | | 10/1998 | Chance ....................... 600/473 |
| 5,845,639 A | * | 12/1998 | Hochman et al. ........... 600/407 |
| 6,096,510 A | * | 8/2000 | Hochman ..................... 435/29 |
| 6,128,517 A | | 10/2000 | Maki et al. .................. 600/310 |
| 6,161,031 A | * | 12/2000 | Hochman et al. ........... 600/407 |
| 6,196,226 B1 | * | 3/2001 | Hochman et al. ........... 600/425 |
| 6,233,480 B1 | * | 5/2001 | Hochman et al. ........... 600/476 |
| 6,241,672 B1 | * | 6/2001 | Hochman et al. ........... 600/431 |
| 6,573,063 B2 | * | 6/2003 | Hochman ..................... 435/29 |

OTHER PUBLICATIONS

Doughtery, Thomas J., et al. "Photoradiation Therapy For The Treatment Of Malignant Tumors," *Cancer Research*, vol. 38, pp. 2628–2635,1(Aug., 1978).

Doiron et al. "Fluorescence Branchoscopy For Detection," *Chest*, vol. 76, No. 1, pp. 27–32 (Jul., 1979).

Palcic et al. "Development of lung imaging device fluorescence endoscope," *IEEE Engineering in Medicine & Biology, Annual Conference Proceedings* 12(1):0196–0197, 1990.

Baumgartner et al. "A fluorescence imaging device for endoscopic detection of early stage cancer: instrumental and experimental studies," *Pergamon Journals Ltd.*, 513–517, 1987.

Chance, B. et al., "Highly Sensitive Object Location In Tissue Models With Linear In–Phase And Anti–Phase Multi–Element Optical Arrays In One And Two Dimensions," *Proc. Nat'l. Acad. Sci.*, vol. 90, pp. 3423–3427 (Apr., 1993).

Herbin, M., et al., "Automated Registration Of Dissimilar Images: Application To Medical Imagery," pp. 77–88 (1989).

D'Orsi, Carl J., et al. "Lightscanning Of The Breast," "*Breast Cancer Detection*",*Grune & Stratton, Inc.*, pp. 169–177 (1987).

Grinvald et al. "High–resolution optical imaging of functional brain architecture in the awake monkey," *Proc. Nat'l Acad. Sci. USA* [ ]:11559–11563, 1991.

Grinvald, Amiram, et al. , "Optical Imaging Of Neuronal Activity," *Physiological Reviews*, vol. 68, No. 4, pp. 1285–1366 (Oct., 1988).

Ts'o, Daniel Y., et al., "Functional Organization Of Primate Visual Cortex Revealed By High Resolution Optical Imaging," *Science*, vol. 249, pp. 417–420 (1990).

Frostig et al. "Cortical Functional Architecture And Local Coupling Between Neuronal Activity And The Microcirculation Revealed By In Vivo High–Resolution Optical Imaging Of Intrinsic Signals," *Proc. Nat'l. Acad. Sci.*, vol. 87, pp. 6082–6086 (Aug., 1990).

McCormick et al. "Noninvasive Cerebral Optical Spectroscopy for Monitoring Cerebral Oxygen Delivery and Hemodynamics," *Critical Care Medicine*, vol. 19, No. 1, pp. 89–97 (Jan., 1991).

Haglund, Michael M., "Video Imaging Of Neuronal Activity," pp. 85–111.

Webb, S.J., et al., "Microwave Absorption By Normal And Tumor Cells," *Science*, vol. 174, pp. 72–74 (Oct., 1971).

Grinvald, Amiram, et al. "Functional Architecture Of Cortex Revealed By Optical Imaging Of Intrinsic Signals," *Nature*, vol. 324, pp. 361–364 (Nov., 1986).

Grinvald "High–Resolution Optical Imaging of Functional Brain Architecture in the Awake Monkey," pp. 11559–11563 (Jun., 1991).

Blasdel, Gary G., et al. ,"Voltage–Sensitive Dyes Reveal A Modular Organization In Monkey Striate Signals," *Nature*, vol. 321, No. 6070, pp. 579–585 (Jun., 1988).

PCT International Search Report; In re Hochman, Daryl; International Application No. PCT/US00/21063, filed Aug. 2, 2000.

Kinsey et al., *Endoscopic System for simultaneous visual examination and electronic detection of fluorescence*, *Rev.Sci.Instrum.* 51:10, 1403–06, 1980.

Dougherty et al.,*Photoradiation Therapy for the Treatment of Malingnant Tumors* Cancer Research 38, 2628–33, 1978.

Doiron et al., *Fluorescence Branchoscopy for Detection*, Chest 76:1, 27–32, 1979.

B. Palcic et al., *Development of a Lung Imaging Fluorescence Endoscope*, Annual Intl Conf./IEEE Engrng in Medicine&Biology Society 12:1 0196–7, 1990.

Baumgartner et al., *A Fluorescence Imaging Device for Endoscopic Detection of Early State Cancer—Instrumental and Experimental Studies*, Pergamon Journals Ltd., 513–517, 1987.

Chance et al., Proc. Natl. Acad. Sci. USA 90:3423, 1993, "Highly sensitive object location in tissue models".

D'Orsi et al., L.W. Bassett and R.H. Gold eds., Breast Cancer Detection, Mammography and Other Methods in Breast Imaging, 2nd ed., Grune & Stratton, Inc., 1987; pp. 169–177.

Ts'o et al., Science 249:417, 1990.

Frostig et al., Proc. Natl. Acad. Sci. USA 87:6082, 1990; "Cortical functional architecture and local coupling between neuronal activity and the microcirculation revealed by in vivo high–resolution optical imaging".

Haglund and Blasdel, "Video Imaging of Neuronal Activity", pp. 85–111; undated.

Herbin et al, "Automated Registration of Dissimilar Images: Application to Medical Imagery", pp. 77–88, 1989.*

Grinvald et al., "High–resolution optical imaging of functional brain architecture in the awake monkey", pp. 11559–11563, 1991; Proc. Nat'l Acad. Sci. USA.*

Grinvald et al.,"Optical imaging of Neuronal Activity", Physiological Reviews, vol. 68, No. 4, pp. 1285–1366, 1988.*

McCormick et al., "Intracerebral penetration of infrared light", J. Neurosurg. vol. 76, pp. 315–318, Feb. 1992.*

Herbin et al.; "Automated Registration of Dissimilar Images: Application to Medical Imagery", pp. 77–88, 1989.

D'Orsi et al., in L.W. Bassett and R.H. Gold eds., *Breast Cancer Detection, Mammography and Other Methods in Breast Imaging*, 2nd ed., Grune & Stratton, Inc., 1987; pp 169–177.

Grinvald et al., Proc. Natl. Acad. Sci. USA __:11559; 1991; "High resolution optical imaging of functional brain architecture in the awake monkey".

Ts'o et al., Science 249:417, 1990, "Functional Organization of Primate Visual Cortex Revealed by High Resolution Optical Imaging".

Frostig et al., Proc. Natl. Acad. Sci. USA 87:6082, 1990; "Cortical functional architecture and local coupling between neural activity and the microcirculation revealed in vivo high–resolution optical imaging of intrinsic signals".

"Microwave Absorption by Normal and Tumor Cells", *Science*, vol. 174, pp. 72–74.*

"A Nonaliasing, Real–Time Spatial Transform Technique", by Karl M. Fant, 1/86.

"Optical Imaging of Neuronal Activity", Physiological Reviews, vol. 68, No. 4, Oct. 1988, by Grinvald, et al., pp. 1235–1367.

"Basic Mechanisms Implicated in Surgical Treatments of Epilepsy" by Ojemann, George A., 1980, pp. 261.277.

"Functional Organization of Primate Visual Cortex Revealed by High Resolution Optical Imaging", Ts'O et al. pp. 417–420. *Science*, Jul. 27, 1990.

"Optical Imaging of Cortical Activity: Real–Time Imaging Using Extrinsic–signals and, high resolution imaging based on sloe intrinsic–signals"pp. 543–559, Lieke et al; Annul. Rev. Physiol. 1989.

"Functional Architecture of Cortex Revealed by Optical Imaging of Intrinsic Signals", by Grinvald et al., *Nature*, Nov. 27, 1986, pp. 361–364.

"Voltage–Sensitive Dyes Reveal a Modular Organization in Monkey Striate Cortex" by Blasdel, et al, pp. 579–585, *Nature* Jun. 5, 1986.

"Optical Imaging of Neuronal Activity in the Visual Cortex", by Grinvald pp. 117–136. *Neural Mechanisms* of Visual Perception.

* cited by examiner

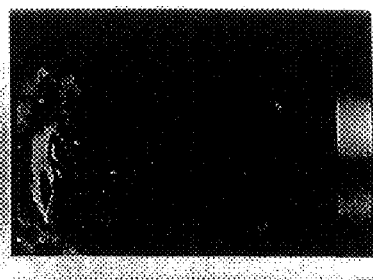
FIGURE 7A FIGURE 7B FIGURE 7C
FIGURE 7D FIGURE 7E FIGURE 7F

METHODS AND SYSTEMS FOR DETECTING ABNORMAL TISSUE USING SPECTROSCOPIC TECHNIQUES

CROSS REFERENCE TO RELATED APPLICATIONS

This patent application is a continuation-in-part of U.S. patent application Ser. No. 08/993,733, filed Dec. 18, 1997 now U.S. Pat. No. 6,241,672, which is a continuation of U.S. patent application Ser. No. 08/477,468, filed Jun. 7, 1995 and issued as U.S. Pat. No. 5,699,798, which is a continuation-in-part of U.S. patent application Ser. No. 08/073,353, filed Jun. 7, 1993 and issued as U.S. Pat. No. 5,465,718, which is a continuation-in-part of U.S. patent application Ser. No. 07/894,270, filed on Jun. 8, 1992 and issued as U.S. Pat. No. 5,438,989, which is a continuation-in-part of U.S. patent application Ser. No. 07/565,454 filed on Aug. 10, 1990 and issued as U.S. Pat. No. 5,215,095, all of which are incorporated herein by reference in their entireties.

TECHNICAL FIELD OF THE INVENTION

The present invention relates to methods and systems for detecting abnormalities, such as cancer and pathological conditions, in cells and tissues using optical, or spectroscopic techniques.

More specifically, the methods and apparatus of the present invention relate to the use of contrast enhancing agents in connection with optical spectroscopic techniques to distinguish abnormal or pathological tissue, such as cancerous tissue, from normal tissue and to grade and characterize cancerous tissue.

BACKGROUND OF THE INVENTION

Methods and systems for identifying abnormal or pathological cells and tissue, particularly cancer, and for diagnosing cancerous conditions, are generally time consuming and invasive. Furthermore, many of the screening techniques currently available provide limited sensitivity and specificity. Tissue biopsies or samples may be taken, fixed and examined using various histological techniques. Since these diagnostic procedures are both invasive and expensive, and they are very stressful for patients undergoing testing, it is desirable to screen areas of suspected abnormalities first, to eliminate unnecessary trauma and expense. Diagnostic screening techniques used for detecting breast cancer, uterine and cervical cancers, colon and colo-rectal cancers, esophageal cancer and skin cancers are generally inadequate and unreliable. It is thus a high priority to develop methods and systems providing reliable, non-invasive screening techniques for identifying cancer cells that have a high degree of sensitivity and specificity.

The diagnostic value of performing a biopsy is dependent upon the selection of tissue for sampling. Many pathologies are not uniformly distributed and, therefore, the selection of tissue for sampling may be determinative of the diagnostic outcome. Additionally, unnecessary removal of tissue may result in localized trauma and, in some cases, may result in diminished function. Taking tissue samples from lymph nodes, for example, is essential to assess the progression of many cancers. Yet, removal of too much tissue, or removal of normal localized tissue having a specialized function may result in diminished function. It is therefore essential to identify and sample tissue that has the highest likelihood of including pathological cells, while avoiding the removal of healthy tissue.

A primary means for treatment of pathologies, such as cancer, is surgical removal. Many studies have shown that the clinical outcome is improved when more of the total amount of tumor tissue is removed. For gross total resections of tumors, the five year survival rate is significantly increased compared to subtotal resection. Both duration of survival and independent status of the patient are prolonged when the extent of resection is maximized in cancerous tissue. Current intraoperative techniques do not provide rapid differentiation of tumor tissue from normal surrounding tissue, however, particularly after resection of the tumor begins. Development of techniques that enhance the ability to identify tumor tissue intraoperatively may result in maximizing the degree of tumor resection, thereby prolonging survival.

Most current tumor detection techniques are performed prior to surgery to provide information about tumor location. Pre-surgical imaging methods include magnetic resonance imaging (MRI) and computerized tomography (CT). In the operating room, intraoperative ultrasound and stereotaxic systems provide information about the location of tumors. Ultrasound shows the location of the tumor from the surface but, once surgery begins, ultrasound techniques do not provide information sufficient to prevent the destruction of important functional tissue while permitting maximal removal of tumor tissue. Stereotaxic systems coupled with advanced imaging techniques have, at select hospitals, provided localization of tumor margins based upon the preoperative CT or MRI scans. However, studies have shown that the location of the tumor changes, particularly during invasive surgeries, and the actual tumor may extend 2–3 cm beyond where the image enhanced putative tumor is located on preoperative images.

One method currently available for determining the location of tumors is to obtain multiple biopsies during surgery and wait for results of microscopic examination of sections. This technique, known as multiple histological margin sampling, suffers several drawbacks. First, this is a time-consuming procedure and can add about 30 to 90 minutes (depending upon the number of samples taken) to the length of time the patient is under anesthesia. The increased time required for margin sampling leads to increased medical costs, as operating room time costs are high. Moreover, increased operating room time for the patient increases the probability of infection and complications arising from the anesthesia. Multiple histological margin sampling is prone to errors, as the pathologist must prepare and evaluate samples in short order. In addition, margin sampling does not truly evaluate all regions surrounding a primary tumor and some areas of residual tumor can be missed due to sampling error.

Thus, although patient outcome is dependent upon aggressive removal of tumor tissue, a surgeon often does not have reliable intraoperative information concerning the location and extent of the tumor. Surgeons must make difficult decisions between aggressively removing tissue and destroying surrounding functional tissue, and they may not know the true outcome of the procedure until permanent tissue sections are available about one week later. Additional surgical procedures may be required following examination of the histological studies.

Other techniques developed to improve imaging of solid tumor masses during surgery include determining the shape of visible luminescence spectra from normal and cancerous tissue. U.S. Pat. No. 4,930,516 teaches that the shape of visible luminescence spectra from normal and cancerous tissue are different. Specifically, there is a shift to blue with different luminescent intensity peaks in cancerous tissue as compared to normal tissue. Thus it is possible to distinguish cancerous tissue by exciting the tissue with a beam of ultraviolet (UV) light and comparing visible native luminescence emitted from the tissue with luminescence from a non-cancerous control of the same tissue type. Such a procedure is fraught with difficulties since a real time, spatial map of the tumor location is not provided for the use of a surgeon. Moreover, the use of UV light at an excitation wavelength can cause photodynamic changes to normal cells and is dangerous for use in an operating room. In addition, UV light penetrates only superficially into tissue and requires quartz optical components instead of glass.

Following the identification and localization of malignant tissue, or following surgical removal of malignant tissue, it is important to monitor the tissue in the area of malignancy for the reappearance or spreading of malignant tissue. Similarly, monitoring an area of interest such as malignant tissue during and/or following treatment with drugs, radiation therapy, or the like, is necessary to assess the efficacy of the treatment and to monitor the progression or recession of the malignancy. Convenient, inexpensive and minimally invasive techniques are desirable for performing these monitoring functions, and few effective systems are available.

U.S. Pat. No. 5,438,989 discloses a method for imaging margins, grade and dimensions of solid tumor tissue by illuminating the area of interest with high intensity electromagnetic radiation containing a wavelength absorbed by a contrast agent, obtaining a background video image of the area of interest, administering a contrast agent, and obtaining subsequent video images that, when compared with the background image, identify the solid tumor tissue as an area of changed absorption. U.S. Pat. No. 5,699,798 discloses methods and apparatus for optically distinguishing between tumor and non-tumor tissue, and imaging margins and dimensions of tumors during surgical or diagnostic procedures.

U.S. Pat. No. 5,465,718 discloses a method for imaging tumor tissue adjacent to nerve tissue to aid in selective resection of tumor tissue using stimulation of a nerve with an appropriate paradigm to activate the nerve, permitting imaging of the active nerve. The '718 patent also discloses methods for imaging of cortical functional areas and dysfunctional areas, methods for visualizing intrinsic signals, and methods for enhancing the sensitivity and contrast of images. U.S. Pat. No. 5,845,639 discloses optical imaging methods and apparatus for detecting differences in blood flow rates and flow changes, as well as cortical areas of neuronal inhibition.

SUMMARY OF THE INVENTION

The methods and systems described herein distinguish between normal and abnormal, or pathological tissue, such as cancerous tissue, using optical (spectroscopic) detection techniques and contrast enhancing agents, and aid in identifying pathological tissue during surgical, diagnostic, monitoring and biopsy procedures. For example, optical detection techniques of the present invention may be used in diagnostic screening applications to identify pathological tissue, such as cancerous tissue. In addition, the methods and apparatus of the present invention are used to identify margins and dimensions of pathological tissue during surgical procedures, and to grade and characterize pathological tissue, particularly cancerous tissue. Additionally, methods and systems of the present invention may be used as a biopsy aid to identify potentially abnormal tissue that should be included in a biopsy sample; for monitoring the progression or recession of a pathological condition, such as cancer; and/or for monitoring the efficacy of treatment agents or protocols. The optical detection techniques of the present invention provide information and results in "real-time" and with a high degree of spatial resolution, and thus may be used intraoperatively or be interfaced with stereotaxic systems used during surgical procedures to accurately locate the malignant tissue during surgeries.

The use of contrast-enhancing agents provides data having high sensitivity and specificity, and thus enhanced reliability, and is therefore preferred in conjunction with implementation of the methods and systems described herein. Contrast enhancing agents provide differential optical contrast between normal, functional, and pathological tissue, providing differential contrast enhancement between normal and abnormal tissue. Thus, using the methods and systems described herein, it is possible to identify and differentiate abnormal or pathological tissue from surrounding normal tissue by detecting changes in the optical properties of a tissue sample in situ.

Contrast enhancing agents suitable for use in the present invention enhance differences in the optical properties, or optical contrast, between normal and abnormal tissue. Administration of contrast enhancing agents may, for example, change optical absorption properties, optical scattering properties, birefringence, or the like, differentially in normal and abnormal cells. Alternatively or additionally, contrast enhancing agents may exhibit different dynamics, such as different perfusion rates, clearance rates, or the like, in normal and abnormal tissue or may sequester preferentially in abnormal tissue. For some applications, it may be desirable to employ multiple contrast enhancing agents, each agent having different spectral properties. The contrast enhancing agents are non-toxic to normal cells and do not interfere with normal metabolic activities at the area of interest.

Examples of contrast enhancing agents include fluorescent and phosphorescent materials, photodynamic dyes, indocyanines, fluoresceins, hematoporphyrins, and fluoresdamines, agents that are used topically, such as iodine, weak acidic and basic agents, and the like. The contrast enhancing agent may be administered intravenously, intraarterially, subcutaneously, topically, or using any route of administration that delivers the agent to the area of interest. Indocyanine green, which has a broad absorption wavelength range and a peak absorption in the range of 730 nm to 840 nm, is a suitable contrast enhancing agent for detection of cancerous tissue in diagnostic and intraoperative procedures. Iodine and weak acidic and basic agents are suitable contrast enhancing agents for topical application and screening for cancerous tissue on the surface of tissue, such as cervical tissue, colo-rectal tissue, intestinal system tissue, and the like. Agents that preferentially sequester in abnormal or pathological tissue may be used. Detectors appropriate for use with the contrast enhancing agents employed with methods and systems of the present invention are well known in the art.

The systems of the present invention employ one or more electromagnetic radiation (emr) optical source(s) for illuminating an area of interest (i.e., an area to be screened or an area believed to contain abnormal or pathological tissue), and one or more optical detector(s) capable of detecting and acquiring data relating to one or more optical properties of the area of interest. The optical source(s) and detector(s) may be selected and located to acquire data relating to optical properties of an area of interest that is exposed, or that underlies skin, tissue, bone, dura, or the like. Epi-illumination and reflective detection are preferred for many applications. For some applications, transillumination techniques are used, following administration of a contrast enhancing agent, to identify abnormalities within a tissue sample in situ, such as a breast.

The optical detector(s) may be used to acquire data for analysis in a static mode, or multiple data sets may be acquired at various time intervals for comparison in a dynamic mode. The optical detector(s) may, for example, acquire control data representing the "normal" or "background" optical properties of an area of interest, and then acquire subsequent data representing the optical properties of an area of interest following administration of a contrast-enhancing agent, or during a monitoring interval. The subsequent data is compared to the control data, or to empirically determined standards, to identify changes in optical properties of corresponding spatial locations in the data set that are representative of normal and abnormal tissue.

Optical source(s) may provide continuous or non-continuous illumination. Various types of optical detectors may be used, depending on the emr source(s) used, the optical property being detected, the type of data being collected, certain properties of the area of interest, the desired data processing operations, the format in which the data is displayed, and the type of application, e.g., intraoperative, diagnostic, biopsy, monitoring, or the like. For some applications, emr sources providing continuous, uniform illumination are preferred, while non-continuous illumination using time domain or frequency domain illumination sources are preferred for some applications.

Changes in optical properties that may be indicative of abnormalities include, for example, reflection, refraction, diffraction, absorption, scattering, birefringence, refractive index, Kerr effect, and the like. The optical source and detection system may be incorporated in an apparatus for use external to the area of interest, or optical detection components may be mounted in an invasive or semi-invasive system, such as an endoscope, laparoscope, biopsy device or probe, or may be provided as individual optical fibers or bundles of optical fibers, or the like.

Numerous devices for acquiring, processing and displaying data representative of one or more optical properties of spatially localized and identified areas in an area of interest can be employed. In general, any type of photon detector may be utilized as an optical detector. The optical detector generally includes photon sensitive elements and optical elements that enhance or process the detected optical signals, such as lenses, polarizers, objectives, and the like. In a simple form, the apparatus of the present invention may include one or more optical fibers operably connected to one or more emr sources that illuminates tissue, with corresponding optical fibers operably connected to an optical detector, such as a photodiode, that detects one or more optical properties of the illuminated tissue. According to another embodiment, a video camera acquires control and subsequent images of an area of interest that can then be compared to identify areas of abnormal tissue. Examination of such data elucidates the precise spatial location of tissue abnormalities and permits characterization of abnormal tissue, such as cancerous tissue. Apparatus and methods suitable for obtaining data relating to one or more optical properties of an area of interest have been described in the patents incorporated herein by reference and are more fully described below.

For most surgical, diagnostic, and monitoring uses, the optical detector preferably provides data having a high degree of spatial resolution at a magnification sufficient to precisely locate the margins of abnormal tissue, such as tumors and cancerous tissue. Several data sets are preferably acquired over a predetermined time period and combined, such as by averaging, to provide data sets for analysis and comparison. Methods and systems of the present invention may be used in a static mode that provides a comparison of optical properties of different spatial locations in an area of interest, to spatially locate areas showing differential contrast enhancement and thereby locate areas of normal and abnormal tissue. A comparison of optical properties of two different areas of interest may also be made in a static mode. Thus, following administration of a contrast enhancing agent, an area of interest believed to contain abnormal tissue may be compared to another area of interest of the same type of tissue believed to contain normal tissue. In this embodiment, the presumed normal area of interest provides the control, or background data set for comparison with the area of interest believed to contain abnormal tissue.

Operation of methods and systems of the present invention in a dynamic mode compares data acquired from corresponding spatial locations at various time points. While it is preferred, for many applications, to acquire control data sets from the area of interest of each patient prior to administration of the contrast enhancing agent to compare with subsequent data sets acquired from the same area of interest in the same patient subsequent to administration of the contrast enhancing agent, it is also possible to compare data sets acquired following administration of a contrast enhancing agent to empirically determined standard or control data sets.

Various data processing techniques may be advantageously used to assess the data collected in accordance with the present invention. Data may be analyzed and displayed in a variety of formats. Processing may include averaging or otherwise combining a plurality of data sets to produce control, subsequent or comparison data sets. Other optical data processing techniques include frequency domain methods such as Fourier or wavelett transformations of the optical data, or spatial domain methods such as convolutions, geometrical transformations, data differencing, and the like.

Data processing may also include amplification of certain signals or portions of a data set (e.g., areas of an image) to enhance the contrast seen in data set comparisons, and to thereby identify areas of abnormal tissue with a high degree of spatial resolution. For example, according to one embodiment, images are processed using a transformation in which data point brightness values are remapped to cover a broader dynamic range of values. A "low" value may be selected and mapped to zero, with all data point brightness values at or below the low value set to zero, and a "high" value may be selected and mapped to a selected value, with all data point brightness values at or above the high value mapped to the high value. Data having an intermediate brightness value, representing the dynamic changes in brightness indicative of changes in optical properties, may be mapped to linearly or logarithmically increasing brightness values. This type of processing manipulation is frequently referred to as a "histogram stretch" or point transformation, and can be used according to the present invention to enhance the contrast of data sets, such as images, representing differences in tissue type.

Data processing techniques may also be used to manipulate data sets to provide more accurate combined and comparison data. For example, patient movement, respiration, heartbeat or reflex activity may shift an area of interest during detection of optical properties and data collection. It is important that corresponding data points in data sets (such as corresponding pixels of an image) are precisely aligned, spatially, to provide accurate combined and comparison data. Such alignment may be accomplished manually by a practitioner having specialized skill and expertise, or using a variety of mechanical and/or mathematical means. Emr source(s) and optical detector(s) may, for example, be mounted in a relatively "fixed" condition in proximity to an area of interest. Optical markers may be fixed at an area of interest and detected as the data is collected to aid in manual alignment or mathematical manipulation. Motion artifacts may be reduced or substantially eliminated by timing the acquisition of data to the cycle of respiration, heartbeat, or the like, to normalize the data. Various processing techniques are described below and in the patents incorporated herein by reference.

Comparison data may be displayed in a variety of ways. For example, comparison data may be displayed in a graphical format that highlights optical differences differentiating normal from abnormal tissue. A preferred technique for presenting and displaying comparison data is in the form of visual images, or photographic frames, corresponding to the area of interest. This format provides a visualizable spatial location (two- or three-dimensional) of an area of interest that is useful for treatment, diagnosis and monitoring.

To enhance and provide better visualization of optical contrast between abnormal and normal tissue, comparison images may be processed to provide an enhanced contrast grey scale or even a color image. A look up table ("LUT") may be provided, for example, that converts the gray scale values for each pixel to a different (higher contrast) gray scale value, or to a color value. Color values may map to a range of grey scale values, or color may be used to distinguish between positive-going and negative-going optical changes. In general, color-converted images provide higher contrast images that highlight changes in optical properties representing areas of malignant and normal tissue.

In operation, an area of interest in a patient is illuminated with electromagnetic radiation (emr) while one or a series of data points or data sets representing one or more optical properties of spatially definable areas in the area of interest is acquired. Data sets are acquired before and/or after the administration of a contrast enhancing agent. The area of interest may be exposed to the emr source(s), or may underlie skin, tissue, bone, dura, or the like, provided that the emr source(s) is selected and positioned to penetrate tissue overlying the area of interest. Alternatively, the area of interest may be located within tissue, and the emr source(s) and detector(s) selected and positioned for transillumination of the area of interest.

For operation in a static mode, a contrast enhancing agent is administered, such as by injection or topical application, to an area of interest, and a data set mapping one or more optical properties to spatial locations in the area of interest is acquired. Spatial locations evidencing contrasting optical properties highlight areas of normal and abnormal tissue. Application of a topical contrast enhancing agent such as iodine or a weak acidic or basic agent to the surface of an area of interest, such as cervical tissue, colo-rectal tissue, digestive system tissue, esophageal tissue, or the like, for example, is followed by illumination of the area of interest and detection of differential optical properties at different spatial locations within the area of interest. Similarly, injections of a contrast enhancing agent, such as indocyanine green, followed by illumination of the area of interest and detection of differential optical properties corresponding to different spatial locations within the area of interest, provides differentiation and spatial localization of abnormal tissue, such as cancerous tissue, from surrounding normal tissue.

Additionally, operation in a static mode may involve illumination and acquisition of data sets from two spatially separated locations and comparison of the data sets at one or more time points following administration of the contrast enhancing agent. Thus, for example, data representative of the optical properties of two different areas of breast tissue may be acquired at predetermined time intervals following administration of a contrast enhancing agent, such as indocyanine green. One of the areas of interest is presumed to contain "normal" tissue. Data from the "normal" area of interest is compared to data from another area of interest to detect and spatially localize differential optical properties that are indicative of abnormal tissue.

Acquired data may be compared to control or background data during operation in a static or a dynamic mode. Control data may represent standards derived from optical properties of empirical data samples of desired tissue populations. Control data may thus be derived representing various normal tissue types as well as various abnormal tissue types, such as different types and grades of tumors. Comparison of data acquired following administration of a contrast enhancing agent to various types of control data may then provide identification and spatial localization of abnormal tissue, such as cancer, as well as typing of the abnormal tissue, such as identifying particular cancers, and grading of cancerous tissue. For abnormalities such as cancer, it may be desirable to compare multiple data sets acquired at intervals following administration of the contrast enhancing agent to control data to observe changes in the optical properties of tissue at the area of interest at predetermined time intervals following administration of the contrast enhancing agent. According to one embodiment, statistically significant, contrast enhanced changes in optical properties of tissue may be determined empirically for various types of tissue, cancers, contrast enhancing agents and the like. Comparison of a data set acquired following administration of a contrast enhancing agent to a control data set representing statistically significant changes provides identification of spatial locations within an area of interest evidencing statistically significant changes indicative of abnormalities.

In another dynamic mode, data acquired corresponding to an optical property of an area of interest prior to administration of a contrast enhancing agent represents control, or background, data. A series of data sets is preferably combined, for example by averaging, to obtain a control data set. The control data set is stored for comparison with data collected subsequently. Alternatively, control or background data corresponding to various conditions of tissue and areas of interest may be acquired, stored, and used for comparison. Control data sets may also be acquired, in real time, from an area of interest believed to contain normal tissue. A subsequent data set representing the corresponding optical property is acquired during a subsequent time period following administration of a contrast enhancing agent. A series of subsequent data sets is preferably combined, for example by averaging, to obtain a subsequent data set. Subsequent data sets are compared with one or more control data set(s) to obtain comparison data set(s), preferably difference data set(s). Comparison data sets are then examined for evidence of changes in optical properties representative of areas of abnormal versus normal tissue within an area of interest.

According to one embodiment, the methods and systems described herein may be employed to obtain three-dimensional information of an area of interest suspected to contain abnormal tissue by: (a) illuminating the area of interest with a least two different wavelengths of emr; (b) obtaining a sequence of control data sets corresponding to each wavelength of emr; (c) administering a contrasting enhancing agent; (d) obtaining a sequence of subsequent data sets for each wavelength of emr; (e) obtaining a series of comparison data sets for each wavelength of light by subtracting the control data set from the subsequent data set or alternatively, in the case of fluorescent dyes, subtracting the subsequent image from the control image; and (f) obtaining an enhanced comparison data set by ratioing the first comparison data set to the second comparison data set. Data corresponding to three dimensional spatial locations may also be acquired using multiple contrast enhancing agents having different spectral properties, and by employing optical tomography techniques. Specifically, photon time-of-flight techniques and frequency domain methods may also be used.

BRIEF DESCRIPTION OF THE DRAWINGS

The patent file contains at least one drawing executed in color. Copies of this patent with color drawings will be provided by the U.S. Patent and Trademark Office upon request and payment of the necessary fee.

The methods and apparatus of the present invention will be described in greater detail below with reference to the following Figures. The file of this patent contains at least one drawing executed in color. Copies of this patent with color drawing(s) will be provided by the Patent and Trademark Office upon request and payment of the necessary fee.

FIG. 7 shows a spatial map of dynamic changes in tumor vs. non-tumor areas in a rat glioma model. These images are of the same animal as shown in FIG. 5; however, the cranium has now been removed so as to expose the left hemisphere containing the glioma, and the right hemisphere containing normal tissue.

FIGS. 11–11C show the effect of the agent furosemide on stimulation-evoked afterdischarge activity in a hippocampal slice comparing the field response measurements at an extracellular electrode, with images highlighting changes in optical properties. Experiments were conducted as described in Example 7.

DETAILED DESCRIPTION OF THE INVENTION

Figure 1A:
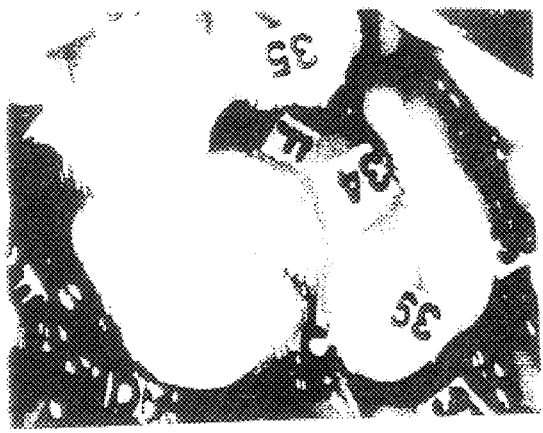
FIG. 1 illustrates the identification of low grade human central nervous system (CNS) tumor tissue using the methods and apparatus of the present invention.

Applicants' optical detection methods and systems are described in greater detail below with reference to certain preferred embodiments. Certain aspects of the optical imaging techniques have been described in even greater detail in the patents incorporated herein by reference. The detailed descriptions of certain preferred embodiments are not intended to limit the scope of the applicant's invention as described herein and set forth in the appended claims. The following terms, as used in this specification and the appended claims, have the meanings indicated:

Area of Interest is an area of tissue that comprises the subject of acquired data sets. In a preferred embodiment, an area of interest is suspected of containing one or more sites of abnormal tissue. In some embodiments, an area of interest is believed to contain normal tissue and data acquired is used as control or background data.

Arithmetic Logic Unit (ALU) is a component that is capable of performing one or more processing (e.g., mathematical and logic) operation(s) (e.g., sum, difference, comparison, exclusive or multiply by a constant, etc.) on a data set.

Control Data is data representing one or more optical properties of an area of interest. Control data may be acquired during a "normal" or a predetermined period, such as prior to administration of a contrast enhancing agent. Control data may also be derived empirically or in real time from one or more "normal" tissue samples. The control data set establishes a "background" profile of optical properties for comparison with a data set acquired following administration of a contrast enhancing agent.

Charge Coupled Device (CCD) is a type of optical detector that utilizes a photo-sensitive silicon chip.

Comparison Data highlights spatial locations within an area of interest having different optical properties. The comparison may be of data points within a single data set, such as different spatial locations within an area of interest. Alternatively, a comparison may be made of data acquired subsequent to administration of a contrast enhancing agent, with control data, such as by adding, subtracting, or the like. The comparison data set is used to identify and/or locate areas of abnormal tissue indicated as areas of enhanced contrast.

Electromagnetic Radiation (emr) means energy having a wavelength of from about 450 to about 2500 nm. Emr illumination suitable for use with the optical detection techniques described herein is in the visible and infrared regions.

Frame is a digitized array of pixels.

Frame Buffer is a component that provides storage of a frame, such as a control image, a subsequent image or a comparison image.

Geometric Transformations can be used to modify spatial relationships between data points in a data set, such as pixels in an image. Geometric transformations are often called "rubber sheet transformations" because they can be viewed as the process of "printing" data, such as an image, on a sheet of rubber and stretching the sheet according to a predefined set of rules. As applied to optical detection, subsequent data sets can be viewed as having been distorted due to movement and it is desirable to "warp" these data sets so that they are spatially aligned with the control images. Geometric transformations are distinguished from "point transformations" in that point transformations modify a data point's (pixel's) value in a data set (an image) based solely upon that data point's (pixel's) value and/or location, and no other data point (pixel) values are involved in the transformation. Geometric transformations are described in Gonzalez and Wintz, *Digital Image Processing*, Addison-Wesley Publishing Co.: 1987.

Image is a frame or composition of frames representing one or more optical properties of an area of interest.

Optical Properties relate to various properties detectable in the useful range of emr (450–2500 nm) including, but not limited to, scattering (of various types), reflection, refraction, diffraction, absorption and extinction, birefringence, refractive index, Kerr effect and the like.

Optical Source is a device that illuminates an area of interest, permitting optical detection.

Optical Detector is a device capable of detecting one or more desired optical properties of an area of interest. Suitable optical detectors include any type of photon detector, such as photodiodes, photomultiplier tubes, cameras, video cameras, CCD cameras, and the like.

Optical Detection refers to the acquisition, and/or comparison, processing and display of data representative of one or more optical properties of an area of interest. Optical detection may involve acquisition, processing and display of data in the form of images, but need not.

Pixels are the individual units of an image in each frame of a digitized signal. The intensity of each pixel is proportional to the intensity of illumination before signal manipulation and corresponds to the amount of emr (photons) being scattered from a particular area of tissue corresponding to that particular pixel. An image pixel is the smallest unit of a digital image and its output intensity can be any value. A CCD pixel is the smallest detecting element on a CCD chip and its analog output is linearly proportional to the number of photons it detects.

Subsequent Data is data representing one or more optical properties of an area of interest during a monitoring period or subsequent to administration of a contrast enhancing agent.

Methods and systems of the present invention utilizing optical techniques and involving the administration of a contrast enhancing agent to identify and localize abnormal tissue may be implemented for numerous applications. According to one embodiment, optical detection techniques used in conjunction with the administration of a contrast enhancing agent, are used for diagnostic purposes to screen an area of interest to identify whether abnormal tissue, specifically cancerous tissue, is present in the area of interest and, if so, to locate the cancerous tissue with a high degree of spatial resolution. These diagnostic techniques may be used for examining an area of interest that is directly exposed to emr source(s) and detector(s), such as an area of interest exposed during a surgical procedure, or an area of interest exposed to an invasive or semi-invasive instrument, such as a laproscope, endoscope, probe, fiber optic cables, or the like. In this fashion, methods and systems of the present invention may be used for diagnosis of various abnormalities, including cancers of the digestive system organs, including esophageal cancers, colorectal cancers, and the like; skin; reproductive organs, such as prostate, ovarian, uterine and cervical cancers, breast cancer; brain cancer; cancers of the lymphatic system and bone; and the like.

For some applications where the area of interest is directly exposed to emr source(s) and detector(s), permitting epi-illumination of the area of interest, topical application of a contrast enhancing agent may be preferred to other types of delivery systems. Thus, for example, topical application of a contrast enhancing agent such as iodine, or a weak acid or base such as weak acetic acid, to an area of interest such as cervical tissue, or to a surface of an organ or tissue, is followed by acquisition of one or more data sets indicative of one or more optical properties of the area of interest. Comparison of data points within the data set acquired following application of the contrast enhancing agent highlights areas of enhanced optical change and thereby highlights the location of abnormal tissue. Comparison of data set(s) acquired following administration of the contrast enhancing agent to control data indicative of one or more optical properties of normal tissue of the same type, or to control data acquired at the area of interest prior to application of the contrast enhancing agent, provides identification and spatial localization of abnormal tissue, particularly cancerous tissue, by highlighting the different optical properties of the tissue following administration of the contrast enhancing agent.

For other applications, the area of interest underlies skin, bone, tissue, dura, or the like and the emr source(s) provides longer wavelengths of emr that penetrate the overlying tissue to illuminate the area of interest. In general, emr in the near infrared range penetrates tissues sufficiently to provide illumination of areas of interest underlying skin, bone, dura and the like. According to one implementation of methods and systems of the present invention, an area of interest located or embedded within tissue may be examined by transilluminating the area of interest following administration of a contrast enhancing agent. This type of system is useful when a tissue surface overlying the area of interest can be illuminated with emr at a wavelength and at an intensity such that the emr travels through the area of interest and exits a tissue sample, and detectors can be arranged and positioned to detect the emr transmitted through the area of interest. This type of system is particularly useful for non-invasive detection or monitoring of cancerous tissue in breast tissue.

In one embodiment, a contrast enhancing agent is administered to provide perfusion of the area of interest. Initial detection of the contrast enhancing agent is manifest in many types of cancer tissue first, because many contrast enhancing agents perfuse more rapidly into cancerous tissue than normal tissue. Solid tumor margins are generally the first morphological indications of cancer tissue detected by comparison of a control or background data set with a data set acquired from an area of interest containing cancerous tissue following administration of a contrast enhancing agent. In applications in which comparison data is output as an image and the detector is, for example, a camera, a comparison image shows darkened lines outlining a solid tumor mass.

Additionally, many contrast enhancing agents are cleared more slowly from cancerous tissue compared to non-cancerous, normal tissue. After the contrast enhancing agent has perfused throughout the area of interest in both normal tissue and tumor tissue, clearance of the contrast enhancing agent from tumor tissue is delayed compared to clearance of the contrast enhancing agent from normal, non-tumor tissue. This characteristic of the dynamics of perfusion of contrast enhancing agents in tumor compared to non-tumor tissue provides additional opportunities to identify and localize tumor tissue over the course of clearance of the contrast enhancing agent from the area of interest. Additionally, the more aggressive the tumor (higher tumor grade), the longer the contrast enhancing agent remains in the tumor tissue. It is therefore possible to grade malignant tissue using methods and systems of the present invention based on the rate of clearance of the contrast enhancing agent from the area of interest.

Methods and systems of the present invention may also be used to assist in the selection of tissue samples for biopsy. The selection of the biopsy sample is critical—every effort should be made to enhance the likelihood of including abnormal tissue. Yet, tissue biopsies are invasive and may affect important tissues, and therefore should be limited to reduce trauma and preserve function of the tissue. Lymph nodes are frequently biopsied, for example, in an effort to evaluate the extent and progression of various cancers. Administration of a contrast enhancing agent followed by illumination and optical detection to identify and spatially localize areas of abnormal tissue greatly aids in the selection of tissue samples to biopsy. Specifically, with the aid of an optical contrast enhancing agent and the optical techniques of the present invention, the likelihood of obtaining a biopsy sample including abnormal tissue is substantially increased. Optical source(s) and detector(s) may be incorporated in an invasive or non-invasive biopsy instrument, and the contrast enhancing agent may be administered in situ or in another fashion that provides application of the contrast enhancing agent in the area of interest.

Yet another application for methods and systems of the present invention involves in situ monitoring an area of interest to evaluate the progression, or recession, of a condition involving abnormal tissue, such as pathological or tumor tissue, in an area of interest, and to monitor, in situ, the effect of a treatment regimen or agent on an identified or suspected area of interest, such as a tumor. Methods and systems of the present invention may be employed, for example, to provide frequent screening or monitoring of cancerous tissue to rapidly detect any progression that would benefit from additional or different treatment agents or regimen. Screening and monitoring may also be implemented to evaluate the need for additional testing using more expensive and less accessible techniques, such as MRI.

Diagnostic and monitoring procedures involve administration of a contrast enhancing agent to an area of interest, followed by illumination and detection of one or more optical properties of the area of interest. A data set may be examined to identify areas of differential optical properties that may be indicative of normal or abnormal tissue. Comparison of data set(s) representing one or more optical properties of spatially defined locations in the area of interest following administration of the contrast enhancing agent may be made as described above. Such comparisons are preferably made continuously or at predetermined intervals following administration of the contrast enhancing agent to provide information relating to the time course of differential optical properties enhanced by the contrast enhancing agent at the area of interest.

The interaction between the emr and the contrast enhancing agent depends upon the specific agent being used. For example, in the case of a fluorescent dye, the preferred wavelength of emr is one which excites the dye, thereby causing fluorescence. However, for many contrast enhancing agents, such as indocyanine green, the preferred wavelength of emr is one which is absorbed by the dye.

The inventive methods and systems are superior to established tumor detection and localization techniques, such as MRI, because they are capable of distinguishing low grade tumors that cannot be distinguished using current MRI techniques. Additionally, updated comparison data sets may be provided on a continuous or frequent basis during a surgical procedure, for example, by readministering the contrast enhancing agent. The agent may be administered on multiple occasions during a surgical procedure after resection has begun, for example, to examine resected walls for residual tumor tissue. For CNS tumors, MRI techniques can only image advanced stage tumors that have compromised the blood brain barrier. The present optical detection techniques, in contrast, are capable of detecting even low grade tumors that have not yet compromised the blood brain barrier. Methods and systems of the present invention may be implemented using readily available equipment and provided at a substantially lower cost than traditional MRI and CT techniques. Methods and systems of the present invention are also preferable to existing X-ray techniques for screening for breast cancer because they identify and locate cancerous tissue with substantially improved sensitivity and specificity.

The contrast enhancing agent may be any agent that provides differential contrast enhancement between normal and abnormal tissue. Emr-absorbing and fluorescent agents are suitable. Contrast enhancing agents having a short half-life are preferred for some applications, such as intraoperative applications. During surgical resection of a solid tumor, it is important that the agent be rapidly cleared from the area of interest so that additional doses of the contrast enhancing agent can be administered repeatedly to image residual tumor tissue. Agents suitable for use with the present invention include indocyanines, fluoresceins, hematoporphyrins, fluoresdamine and other dyes used for photodynamic treatment of tumor tissue, such as those available from Quadra Logic Technologies, Inc., iodine and weak acidic and basic agents (Vancouver, B.C.). Specific examples of agents which may be usefully employed with the present invention include indocyanine green, Photofrin®, NPe$_6$, BPD, Evans Blue, Biodipy® (available from Molecular Probes, Inc., Eugene, Oreg.) and combinations thereof. The delta 1,2 bicyclo [4,4,0] and delta.sup. 1,6 bicyclo [4,4,0] functional dyes disclosed in U.S. Pat. Nos. 5,672,332 and 5,672,333 and similar agents may also be used with methods and systems of the present invention.

Yet another aspect of the inventive method and systems involves using an emr absorbing or fluorescent dye conjugated to a targeting molecule, such as an antibody, hormone, receptor, or the like. According to one embodiment, the targeting molecule is a monoclonal antibody or fragment thereof specific for an antigen surface marker of a tumor cell. When fluorescent agents are used, the area of interest is illuminated with emr containing excitation wavelengths of the fluorescent agent, but not emission wavelengths. This can be accomplished by use of a cutoff filter over the emr source. Preferably, the optical detector is coupled to an image intensifier or micro channel plate (e.g., KS-1381 Video Scope International, Wash D.C.) to increase the sensitivity of the system by several orders of magnitude and allow for visualization of cells having fluorescent dyes attached thereto. Examples of fluorescent dyes that can be conjugated to a targeting molecule include, for example, Cascade Blue, Texas Red and Lucifer Yellow CH from Molecular Probes, Eugene, Oreg.

The inventive methods employ an apparatus comprising a source of emr, an optical detector for acquiring data representative of one or more optical properties of the area of interest, and data processing and display capability. The apparatus may be constructed as an integrated unit, or it may be used as a collection of components. The apparatus will be briefly described with reference to the schematic diagrams of FIGS. 13–15, and various components and features will then be described in greater detail.

Figure 13:
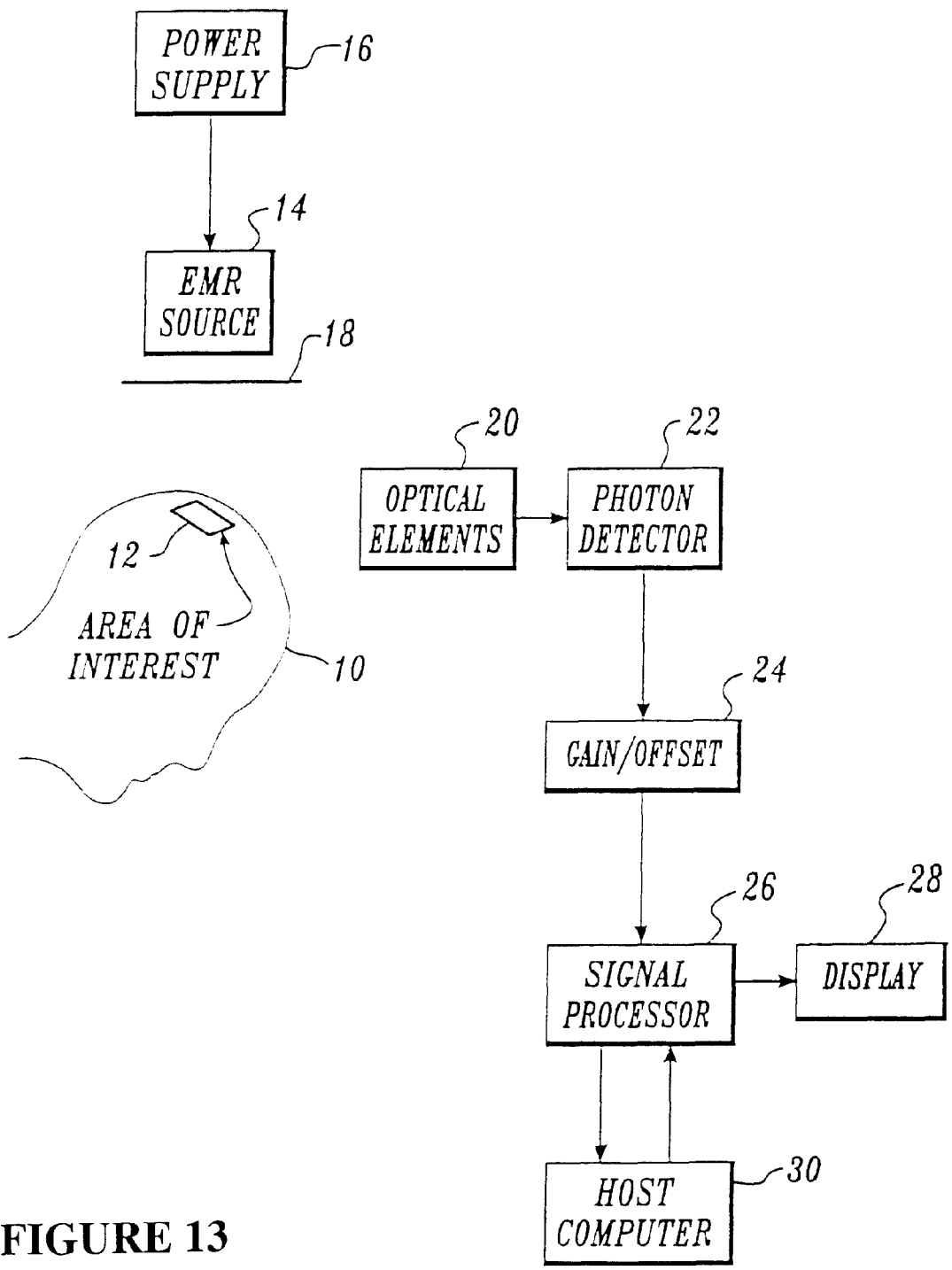
FIG. 13 shows a schematic diagram illustrating an exemplary system of the present invention.

FIG. 13 illustrates a human patient 10 whose neuronal tissue represents area of interest 12. As is described in greater detail below, area of interest 12 may be fully or partially exposed, or detection may be conducted through tissue such as bone and/or dura with proper selection of emr wavelengths. During optical imaging, area of interest 12 is illuminated by emr source 14 powered by regulated power supply 16. Emr is preferably directed through an optical filter 18 prior to contacting area of interest 12.

During optical detection, a light gathering optical element 20, such as a camera lens, endoscope, laparascope, optical fibers, or the like, and photon detector 22 are positioned to detect optical properties of area of interest 12. Signals representative of optical properties are processed, if desired, in a gain, offset component 24 and then conveyed to analog-to-digital (A/D) and digital signal processing hardware 26. Data representing optical properties, and particularly changes in optical properties, is displayed on display device 28. The optical detection, display and processing components are controlled by host computer 30.

Figure 14:
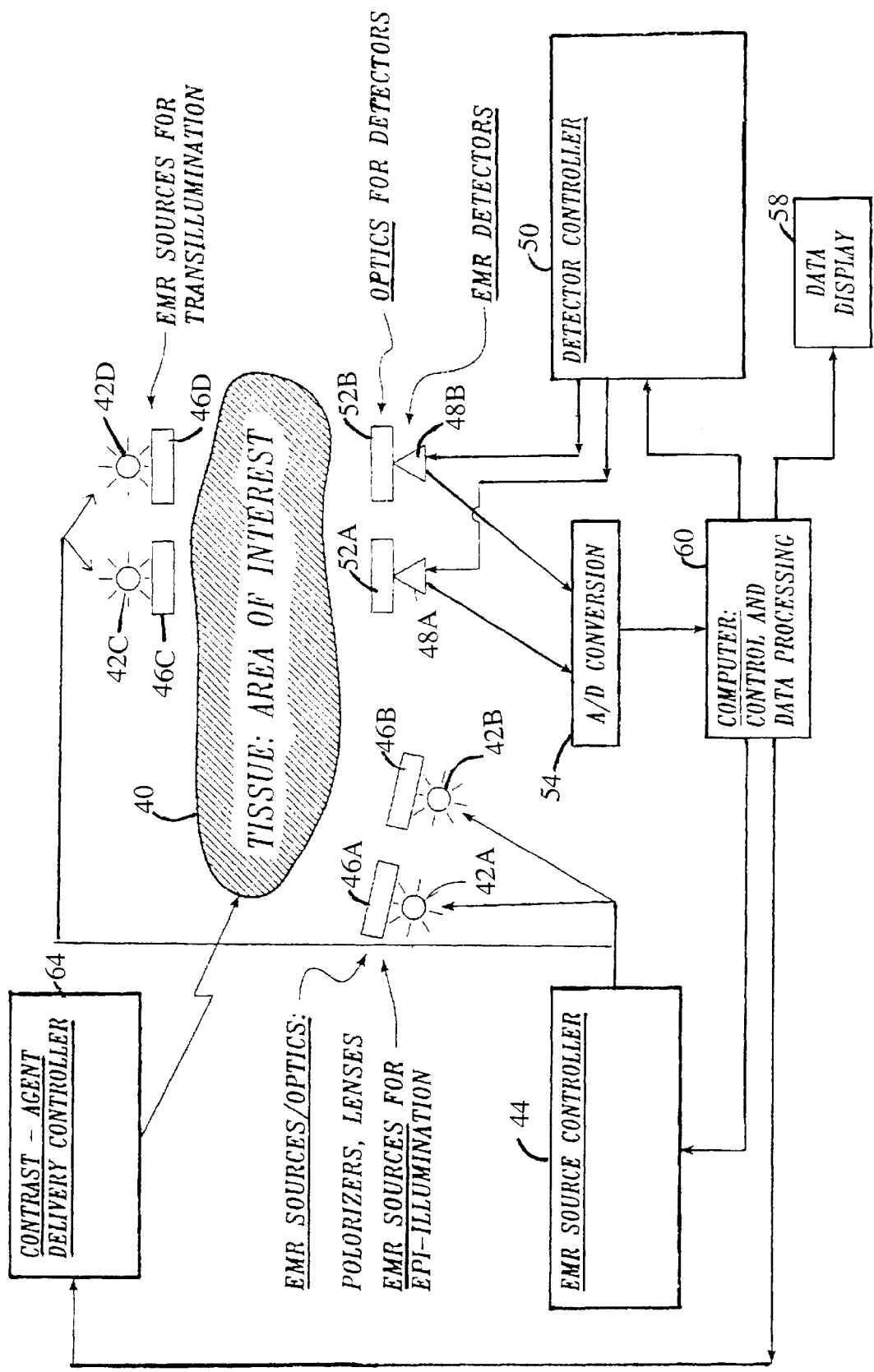
FIG. 14 shows a schematic diagram illustrating exemplary systems of the present invention.

FIG. 14 shows another system of the present invention for operation in an epi-illumination or a transillumination mode. Tissue sample 40 represents the area of interest. An array of emr epiillumination sources is represented by sources 42A and 42B controlled by emr source controller 44. Two emr epi-illumination sources are illustrated at 42A, 42B, but any number of emr sources may be used. An alternative array of emr transillumination sources 42C and 42D is controlled by emr source controller 44. Two emr transillumination sources are illustrated at 42C, 42D, but any number of emr sources may be used. Emr source controller 44 may provide controlled intensity, frequency modulation, wavelength modulation, and the like, and is itself controlled by central control and data processing unit 60. The emr illumination emitted by sources 42A–D may be intercepted by various optical elements 46A, 46B, 46C, 46D prior to impingement on the area of interest. Optical elements may include filters, diffusers, polarizers, lenses, and the like. Emr sources or associated optical elements may be spaced from a surface of the area of interest, as shown, or may directly contact the surface of an area of interest. In general, when an area of interest is exposed tissue, it is not necessary for the emr source or associated optical element to contact the area of interest. When the area of interest underlies tissue, such as bone or soft tissue, it may be desirable for the emr source or associated optical elements to contact an exterior surface in proximity to the underlying area of interest.

Emr detectors 48A and 48B are provided for detecting optical properties of spatially identifiable areas of the area of interest during illumination and following administration of a contrast enhancing agent. Two emr detectors are illustrated, but any number of emr detectors may be used. Emr detector controller 50 may provide various controls for data acquisition, including gain, offset, and various timing features, all of which are preferably controlled by central control and data processing unit 60. The emr detectors may be intercepted by various optical elements 52A, 52B prior to impingement on the area of interest. Optical elements may include polarizers, lenses, objectives, and the like. Emr detectors or associated optical elements may be spaced from a surface of the area of interest, as shown, or may directly contact the surface of an area of interest. Data acquired by emr detectors 48A, 48B is preferably converted from an analog to a digital form in A/D converter 54 before processing in central control and data processing unit 60.

Central control and data processing unit 60 may also control related events, such as the rate, timing and delivery of the contrast enhancing agent. As shown schematically in FIG. 14, contrast enhancing agent delivery controller 64 is also controlled by central control and data processing unit 60. Various data processing and control features, which are described in detail herein, may be implemented by central control and data processing unit 60. Output data in a selected format is displayed on data display unit 58. Data may be displayed in the form of a graph or another format that highlights changes in the optical properties of spatial locations within the area of interest. According to a preferred embodiment, data display unit 62 displays a visual image of the area of interest, as described more fully and illustrated below.

Methods and systems of the present invention may be implemented to acquire data in a epiillumination or transillumination mode, as shown, depending on the orientation of emr sources with respect to the emr detectors. For most applications, emr sources are located for epi-illumination or transillumination of the area of interest, but not both. For certain applications, however, it may be advantageous to provide both epi-illumination and transillumination of an area of interest.

Figure 15:
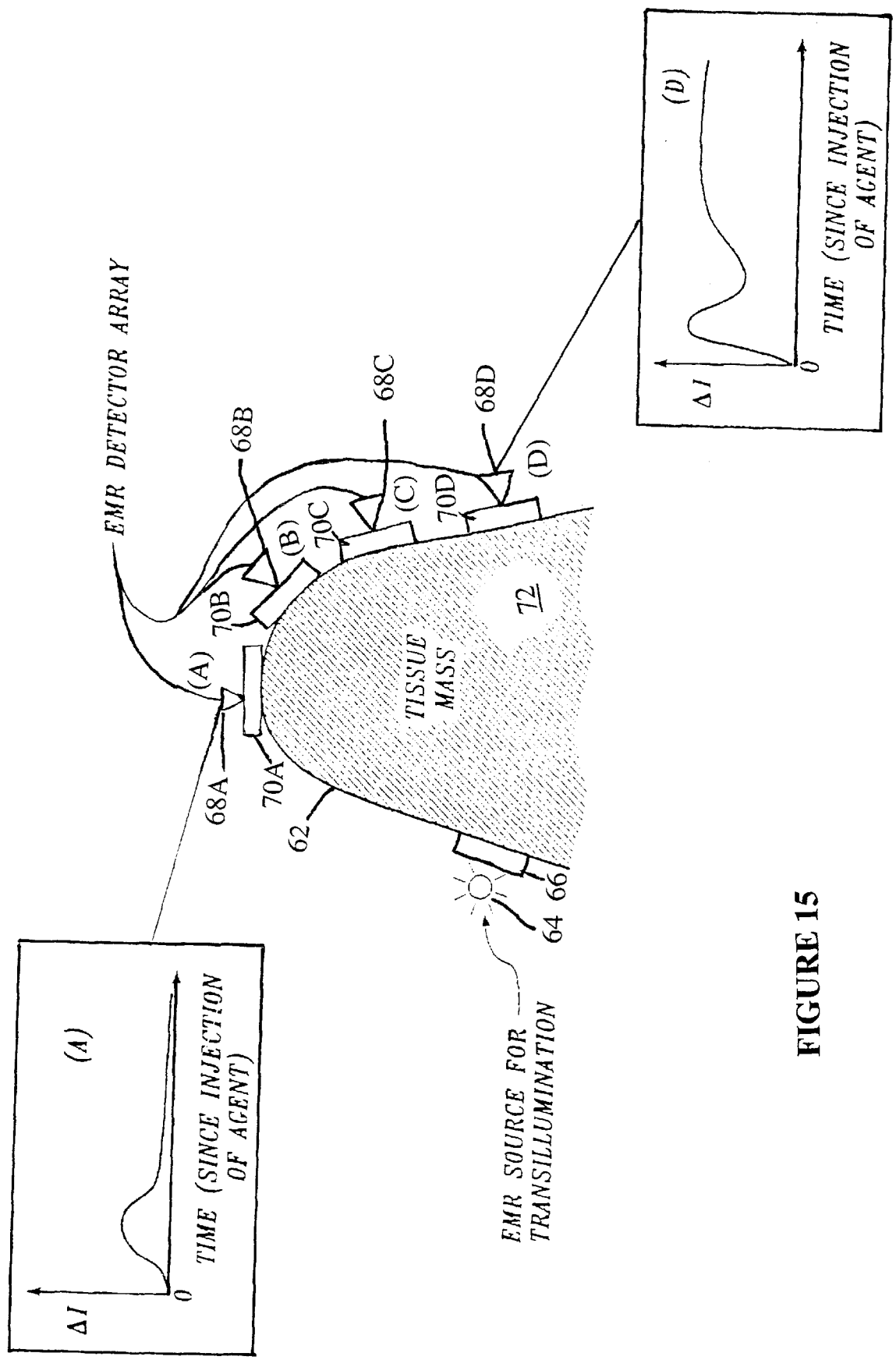
FIG. 15 shows a schematic diagram illustrating the use of optical techniques of the present invention for identifying abnormal tissue.

FIG. 15 shows, schematically, the acquisition of data using methods and systems of the present invention in a transillumination mode, as well as exemplary data output. Tissue mass 62 represents a breast tissue mass. Emr source 64 and appropriate optical elements 66 are selected and positioned for transillumination of the tissue mass. An array of emr detectors 68A–D and appropriate optical elements 70A–D are selected and positioned to detect illumination transitting the tissue mass. Each of the emr detectors is positioned to acquire data from different areas of interest within the tissue mass. An appropriate number and arrangement of emr detectors is preferably provided so that the tissue mass can be screened in its entirety in a single operation. Emr sources and detectors and the appropriate optical elements are controlled and operated as described with reference to FIG. 14.

Following administration of a contrast enhancing agent, such as indocyanine green, data is acquired by each of the emr detectors at predetermined intervals. Plots of the change in intensity of light detected at areas of interest surveyed by emr detectors 68A and 68 D over a time period following administration of the contrast enhancing agent are provided at insets A and D. The data acquired at emr detector 68A, shown in inset A, shows a gradual increase in the change in optical properties evidencing gradual uptake of contrast enhancing agent, followed by a gradual decrease in the change in optical properties, indicating the clearance of the contrast enhancing agent from the area of interest. The data acquired at emr detector 68D, shown at inset D, shows a rapid increase in the change in optical properties shortly after administration of the contrast enhancing agent, followed by a slight decrease in the change in optical properties, followed by a gradual increase and sustained higher level in the change of optical properties in the area of interest. This data is illustrative of a contrast enhanced mass 72, such as a tumor, within tissue mass 62 in proximity to detector 68D, remote from detector 68A. The data from multiple emr detectors may alternatively be combined and output as a visual image that highlights and spatially localizes contrast enhanced masses, such as tumors. Methods and systems of the present invention using contrast enhancing agents may thus be implemented to provide identification and spatial localization of abnormal tissue, such as tumor tissue, in non-invasive manner.

One or more emr source(s) is used for illuminating the area of interest during acquisition of data representing one or more optical properties. The emr source(s) may provide epi-illumination or transillumination, as described above, depending on the relationship between the emr source(s) and detector(s). The emr source(s) may illuminate an area of interest directly, as when tissue is exposed during or in connection with surgery, or it may be utilized to illuminate an area of interest indirectly through adjacent or overlying tissue such as bone, dura, skin, tissue, muscle and the like. Emr sources employed in methods and systems of the present invention preferably provide high intensity illumination. Exemplary emr sources include tungsten-halogen lamps, lasers, light emitting diodes, filtered incandescent sources, and the like. Cutoff filters that selectively pass all wavelengths above or below a selected wavelength may be employed. According to one embodiment, a preferred cutoff filter excludes all wavelengths below about 695 nm. An alternative to using cutoff filters involves administration of a first contrast enhancing agent prior to administration of a second, different contrast enhancing agent that acts as a tissue filter of emr to provide a filter in the area of interest. In this instance, it is desirable to utilize a contrast enhancing agent that remains with tumor or normal tissue for a prolonged period of time. According to another embodiment, illumination is provided through fiber optic strands using a beam splitter controlled by a D.C. regulated power supply (Lambda, Inc.). The emr source(s) may be operated in a continuous illumination mode, or in frequency modulated modes.

Preferred emr wavelengths for use with methods and systems of the present invention include wavelengths of from about 450 nm to about 2500 nm and, most preferably, wavelengths of the near infrared spectrum of from about 700 nm to about 2500 nm. Generally, longer wavelengths (e.g., approximately 800 nm) are employed to analyze deeper areas of tissue. Moreover, if a comparison is made between a data set obtained at 500 nm emr and a data set obtained at 700 nm emr, the difference comparison will show an optical slice of tissue. Selected wavelengths of emr may also be used, for example, when various types of contrast enhancing agents are administered.

According to one embodiment, the area of interest is uniformly illuminated to permit adjustment of the signal over a full dynamic range, as described below. Nonuniformity of illumination is generally caused by fluctuations of the illumination source and intensity variations resulting from the three-dimensional nature of the surface of the area of interest. More uniform illumination can be provided over the area of interest, for example, using diffuse lighting, mounting a wavelength cutoff filter in front of the optical detector and/or emr source, or combinations thereof. Fluctuation of the illumination source itself is preferably addressed by using a light feedback mechanism to regulate the power supply of the illumination source. Additionally, optically transparent plate may contact and cover the area of interest to provide a flatter, more uniform contour. The use of a plate or another mechanical aid to stabilize tissue in an area of interest also diminishes tissue movement during data acquisition. Fluctuations in illumination can be compensated for by using image processing algorithms, including placing a constant shade gray image marker point at the area of interest as a control point.

Methods and systems of the present invention may also usefully employ non-continuous illumination and detection techniques. For example, short pulse (time domain), pulsed time, and amplitude modulated (frequency domain) illumination sources may be used in conjunction with suitable detectors (See Yodh A and Chance B, *Physics Today*, March, 1995). Frequency domain illumination sources typically comprise an array of multiple source elements, such as laser diodes, with each element modulated at 180° out of phase with respect to adjacent elements (See, Chance B et al., *Proc. Natl. Acad. Sci. USA* 90, 3423–3427, 1993). Two-dimensional arrays, comprising four or more elements in two orthogonal planes, can be employed to obtain two-dimensional localization information. Such techniques are described in U.S. Pat. Nos. 4,972,331 and 5,187,672 which are hereby incorporated herein by reference in their entireties.

Time-of-flight and absorbance techniques (Benaron, D A and Stevenson D K, Science 259:1463–1466, 1993) may also be usefully employed in the present invention. In yet another embodiment of the present invention, a scanning laser beam may be used in conjunction with a suitable detector, such as a photomultiplier tube, to obtain high resolution images of an area of interest.

Illumination with a part of the infrared spectrum allows for imaging intrinsic signals through tissue overlying or adjacent the area of interest, such as dura, skull, skin, soft tissue, or the like. One exemplary infrared emr source suitable for imaging through tissue overlying or adjacent the area of interest is a Tunable IR Diode Laser from Laser Photonics, Orlando, Fla. When using this range of far infrared wavelengths, the optical detector is preferably provided as an infrared (IR) detector. IR detectors are made from materials such as indium arsenide, germanium and mercury cadmium telluride, and are generally cryogenically cooled to enhance their sensitivity to small changes in infrared radiation. One example of an IR imaging system which may be usefully employed in the present invention is an IRC-64 infrared camera (Cincinnati Electronics, Mason, Ohio).

One or more optical detector(s) is provided for acquiring a signal representative of one or more optical properties at spatially resolved areas within the of the area of interest. Any photon detector may be employed as an optical detector. Suitable detectors include photodiodes, photo multiplier tubes, photon intensifiers, cameras, video cameras, photon sensitive semiconductor devices, CCD cameras, and the like. Specialized detectors suitable for detecting selected optical properties and having high sensitivity may be employed. One preferred optical detector for acquiring data in the format of an analog video signal is a charge coupled device (CCD) video camera. One suitable device is a CCD-72 Solid State Camera (Dage-MTI Inc., Michigan City, Ind.). Another suitable device is a COHU 6510 CCD Monochrome Camera with a COHU 6500 electronic control box (COHU Electronics, San Diego, Calif.). In some cameras, the analog signal is digitized 8-bits deep on an ADI board (analog-to-digital board). The CCD may be cooled, if necessary, to reduce thermal noise.

Data processing is an important feature of the optical detection techniques and apparatus of the present invention. Optical data processing techniques include frequency domain methods such as Fourier or wavelett transformations of the optical data, spatial domain methods such as convolutions, geometrical transformations, data differencing, and the like.

In use, for example, a CCD apparatus is preferably adjusted (at the level of the analog signal and before digitizing) to amplify the signal and spread the signal across the full possible dynamic range, thereby maximizing the sensitivity of the apparatus. Specific methods for detecting optical signals with sensitivity across a full dynamic range are described in detail in the patents incorporated herein by reference. Means for performing a histogram stretch of the difference frames (e.g., Histogram/Feature Extractor HF 151-1-V module, Imaging Technology, Woburn Mass.) may be provided, for example, to enhance each difference image across its dynamic range. Exemplary linear histogram stretches are described in Green, *Digital Image Processing: a systems approach*, Van Nostrand Reinhold: New York, 1983. A histogram stretch takes the brightest pixel, or the pixel with the highest value in the comparison image, and assigns it the maximum value. The lowest pixel value is assigned the minimum value, and every other value in between is assigned a linear value (for a linear histogram stretch) or a logarithmic value (for a log histogram stretch) between the maximum and minimum values. This allows the comparison image to take advantage of the full dynamic range and provide a high contrast image that clearly identifies areas of tumor tissue.

Noise (such as 60 Hz noise from A.C. power lines)is filtered out in the control unit by an analog filter. Additional adjustments may further enhance, amplify and condition the analog signal from a CCD detector. One means for adjusting the input analog signal is to digitize this signal at video speed (30 Hz), and view the area of interest as a digitized image that is subsequently converted back to analog format.

It is important that data, such as consecutive data sets acquired from of a particular area of interest, be aligned so that data corresponding to the same spatial location is compared. If an averaged control data set and a subsequent data set are misaligned prior to comparison, artifacts will be present and the resulting comparison data set will amplify noise and edge information. Data set misalignment can be caused by patient motion, heartbeat, respiration, and the like. Large patient movements may require realignment of the optical detector and acquisition of a new control data set. It is possible, however, to compensate for small patient or tissue movements using various controls, mechanical or computational means, or a combination of all of these means. The optical detector and emr source may be provided as an integral unit, for example, to reduce relative motion and improve the integrity of data sets. Other techniques for maintaining the optical detector and the illumination source in a constant orientation with respect to the area of interest may also be employed.

Real-time motion compensation and geometric transformations may be used to align corresponding data. Simple mechanical translation of data or more complex (and generally more accurate) geometric transformation techniques can be implemented, depending upon the input data collection rate and amount and type of data processing. For many types of data sets, it is possible to compensate geometrically by translating the image by the x-y plane. In order for an algorithm such as this to be feasible, it must be computationally efficient (preferably implementable in integer arithmetic), memory efficient, and robust with respect to changes in ambient light.

Functional control points can be placed in the area of interest and triangulation-type algorithms used to compensate for movements of these control points. Control points can be placed directly in the area of interest. Goshtasby, "Piecewise Linear Mapping Functions for Image Registration," *Pattern Recognition* 19:459–66, 1986) describes a method whereby an image is divided into triangular regions using control points. A separate geometrical transformation is applied to each triangular region to spatially register each control point to a corresponding triangular region in a control data set.

"Data warping" techniques may be employed whereby each subsequent data set is registered geometrically to the control data set to compensate for movement. Data warping techniques described, for example, in Wolberg, *Digital Image Warping*, IEEE Computer Society Press: Los Alimitos, Calif., 1990, may be used. Data warping techniques may further indicate when movement has become too great for effective compensation and a new control data set must be acquired.

Motion artifacts such as patient respiration, heartbeat or reflex activity may also be reduced or substantially eliminated by timing the acquisition of data to the cycle of respiration, heartbeat, or the like, to normalize the data. Acquisition of data may also be controlled to provide data acquisition at predetermined time points following administration(s) of the contrast enhancing agent.

The data processing function is generally operated and controlled by a host computer. The host computer may comprise any general computer (such as an IBM PC type with an Intel 386, 486 Pentium or similar microprocessor or Sun SPARC) that is interfaced with the emr source and/or optical detector and directs data flow, computations, data acquisition and output, and the like. Thus, the host computer controls acquisition and processing of data and provides a user interface.

According to a preferred embodiment, the host computer comprises a single-board embedded computer with a VME64 interface, or a standard (IEEE 1014-1987) VME interface, depending upon bus band width considerations. Host computer boards which may be employed in the present invention include, for example, Force SPARC/CPU-2E and HP9000 Model 7471. The user interface can be, for example, a Unix/X-Window environment. The processing board can be, for example, based upon Texas Instruments' MVP and other chips providing real-time image averaging, registration and other processing necessary to produce high quality comparison data. According to a preferred embodiment, comparison data is output in an image format. The processing board may also drive, for example, a 120× 1024 RGB display to show a sequence of difference images over time with pseudo-color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, the light source and optical detector control box.

A real-time data acquisition and display system, for example, may comprise four boards for acquisition, image processing, peripheral control and host computer. A minimal configuration with reduced processing capabilities may comprise just the acquisition and host computer boards. The acquisition board comprises circuitry to perform real-time averaging of incoming video frames and allow readout of averaged frames at a maximum rate bus. A VME bus is preferred because of its high peak bandwidth and compatibility with a multitude of existing VME products. The acquisition board should also support many different types of optical detectors via a variable scan interface. A daughter board may support the interfacing needs of many different types of optical detectors and supply variable scan signals to the acquisition motherboard. Preferably, the unit comprises a daughter board interfacing to an RS-170A video signal to support a wide base of cameras. Other camera types, such as slow scan cameras with a higher spatial/contrast resolution and/or better signal to noise ratio, can be developed and incorporated in the inventive device, as well as improved daughter boards to accommodate such improved cameras.

According to a preferred embodiment, data, such as analog video signals, are continuously processed using, for example, an image analyzer (e.g., Series 151 Image Processor, Imaging Technology, Inc., Woburn Mass.). An image analyzer can receive and digitize an analog video signal with an analog to digital interface and perform such a function at a frame speed of about 1/30th of a second (e.g., 30 Hz or "video speed"). Processing the signal involves first digitizing the signal into a series of pixels or small squares assigned a value (in a binary system) dependent upon the number of photons (i.e., quantity of emr) being detected from the part of the area of interest assigned to that pixel. For example, in a standard 512×512 image from a CCD camera, there would be 262,144 pixels per image. In an 8 bit system, each pixel is represented by 8 bits corresponding to one of 256 levels of gray.

The signal processing unit preferably includes a programmable look-up table (e.g., CM150-LUT16, Imaging Technology, Inc., Woburn, Mass.) initialized with values for converting gray coded pixel values, representative of a black and white image, to color coded values based upon the intensity of each gray coded value. This can provide image enhancement via an image stretch. An image stretch is a technique whereby the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise (e.g., glare).

The processing unit may further include a plurality of frame buffers having frame storage areas for storing frames of digitized data received from the analog/digital interface. The frame storage area comprises at least one megabyte of memory space, and preferably at least 8 megabytes of storage space. An additional 16-bit frame storage area is preferred as an accumulator for storing processed image frames having pixel intensities represented by more than 8 bits. The processing unit preferably includes at least three frame buffers, one for storing the control data set, another for storing the subsequent data set, and a third for storing a comparison data set.

According to preferred embodiments, the processing unit further comprises an arithmetic logic unit (e.g., ALU-150 Pipeline Processor) for performing arithmetical and logical functions on data located in one or more frame buffers. An ALU may, for example, provide data averaging in real time. Newly acquired digitized image may be sent directly to the ALU and combined with control data stored in a frame buffer. A 16 bit result can be processed through an ALU, which will divide this result by a constant (i.e., the total number of data sets). The output from the ALU may be stored in a frame buffer, further processed, or used as an input and combined with another image.

The comparison (e.g., difference) data is, preferably, further processed to smooth out the output comparison and remove high frequency noise. For example, a lowpass spatial filter can block high spatial frequencies and/or low spatial frequencies to remove high frequency noise at either end of the dynamic range. This provides a smoothed-out processed difference data set in digital format. The digitally processed difference data set in the form of an image can, for example, be color-coded by assigning a spectrum of colors to differing shades of gray. This image is then converted back to an analog image (by an ADI board) and displayed for a real time visualization of differences between the control data set(s) and subsequent data set(s). Moreover, the processed difference data set can be superimposed over the analog data set to display specific tissue sites where a contrast enhancing agent may have a faster uptake.

Processing speed may be enhanced by adding a real time modular processor or faster CPU chip to the image processor. One example of a real time modular processor which may be employed in the present invention is a 150 RTMP-150 Real Time Modular Processor (Imaging Technology, Woburn, Mass.).

The processing unit may further include an optical disk for storing digital data, a printer for providing a hard copy of the digital and/or analog data and a display, such as a video monitor to permit the physician to continuously monitor the comparison data output.

A single chassis may house all of the modules necessary to provide optical detection of tissue abnormalities according to the present invention. The necessary components, whether or to whatever degree integrated, may be installed on a rack that is easily transportable within and between operating and hospital rooms along with display monitors and peripheral input and output devices. According to another embodiment, optical screening and monitoring devices of the present invention are provided in a modular design integrating a centralized data acquisition, processing and display device with interchangeable optical sources and detectors suitable for use in screening particular areas of interest. Using a modular design, the centralized data acquisition, processing and display device may be used in connection with one set of optical source(s) and detector(s) to assist in tissue sampling, or acquiring a biopsy for diagnostic evaluation in conjunction with one or more optical source(s) and detector(s) adapted for use with or mounted on a biopsy probe or another biopsy source(s) and instrument. Cervical cancer screening or monitoring may be provided using the centralized data acquisition, processing and display device with another set of optical source(s) and detector(s) mountable, for example, on a standard probe or other instrument used in gynecological examinations. Similarly, another set of optical source(s) and detector(s) may be mounted on a laparascope or endoscope and interfaced with the centralized data acquisition, processing and display device to provide screening for abnormal tissues in internal organs and tissues. Yet another set of optical source (s) and detector(s) may be provided for transilluminating an area of interest, such as breast tissue, and interfaced with the centralized data acquisition, processing and display device to detect abnormalities within tissue. Multiple emr sources and detectors for use in a transillumination mode may be interfaced and provided in a flexible arrangement that conforms to the surface contours of the area of interest. Alternatively or additionally, one or more emr sources and detectors may be implanted in an area of interest and interfaced with a centralized data acquisition, processing and display device continuously or at intervals to monitor the area of interest.

The following examples are provided for illustration of specific embodiments and are not intended to limit the methods and systems of the present invention, as described and claimed herein.

EXAMPLE 1

This example illustrates optical detection of a low grade CNS tumor (astrocytoma, grade 1) using the methods and apparatus of the present invention. An MRI scan was conducted before the operation. However, tumors of this type and grade are notoriously difficult to distinguish from normal tissue once the surgical removal of the tumor has begun.

All detection procedures reported in this and in the following examples were reviewed and approved by the University of Washington Human Subjects Review Committee. All patients signed an informed consent form for both the surgery and the detection experiments.

The procedure used in Examples 1–4 was as follows. The area of interest was evenly illuminated by a fiber optic light source with the radiation passing through a beam splitter, controlled by a D.C. regulated power supply (Lambda, Inc.) and passed through a 695 nm longpass filter. Images were acquired with a CCD camera (COHU 6500) fitted to the operating microscope with a specially modified cineadaptor. The cortex was stabilized with a glass footplate. Images were acquired at 30 Hz and digitized at 8 bits (512×480 pixels, using an Imaging Technology, Inc. Series 151 system, Woburn, Mass.). Geometrical transformations were applied to images to compensate for small amounts of patient motion (Wohlberg, *Digital Imaging Warping*, IEEE Computer Society: Los Alamitos, Calif., 1988). Subtraction of images collected following dye administration from those collected during a control state with subsequent division by the control image resulted in percentage difference maps. Raw data (i.e., no digital enhancement) were used for determining the average optical change in specified regions (average size box was 30×30 pixels or 150–250 um$^2$). For pseudocolor images, a linear low pass filter removed high frequency noise and linear histogram transformations were applied. Noise was defined as the standard deviation of fluctuations it! sequentially acquired control images as 0.003–0.009.

Figure 1D:
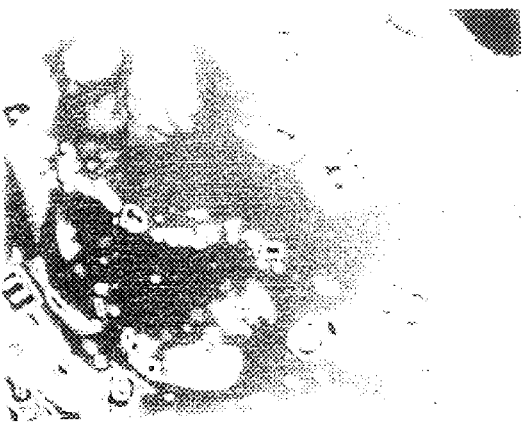
Figure 1B:
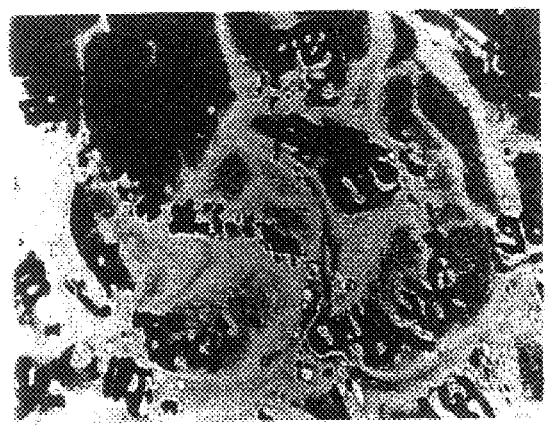
Figure 1E:
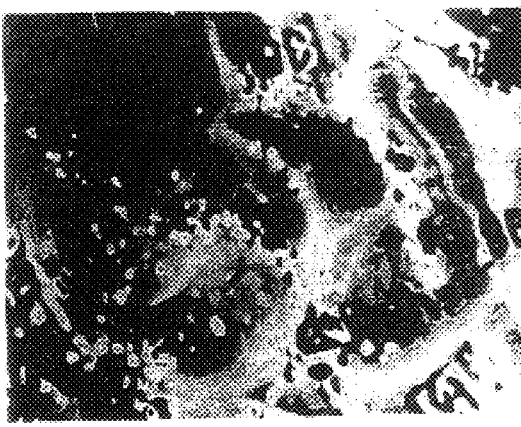
Figure 1C:
Figure 1F:

An averaged control image was obtained of the particular cortical surface area of interest. FIG. 1A is a gray-scale image of the area of interest prior to dye administration. The lettered labels placed upon the brain by the surgeon overlay the tumor as identified intraoperatively by ultrasound. Indocyanine green dye (1 mg/kg) was administered into a peripheral intravenous catheter as a bolus at time 0. FIG. 1B shows a difference image taken approximately 15 seconds after intravenous injection of dye. FIG. 1C shows the difference image about 30 seconds after dye administration. The area of the tumor tissue showed the first tissue staining. FIG. 1D shows that with this low grade tumor, all tissue (both normal and abnormal) showed staining at 45 sec after dye administration. FIG. 1E is an image of the area of interest one minute after dye administration and FIG. 1F is the image five minutes after dye administration showing complete clearance in this low grade tumor. In all the examples presented herein demonstrating optical imaging in humans, each image covers an area of approximately 4 cm×4 cm.

These data show that indocyanine green enters low grade tumor tissue faster than normal brain tissue, and may take longer to be cleared from benign tumor tissue than normal tissue. Therefore, it is possible to image even low grade tumors with this apparatus. Furthermore, it is possible to distinguish low grade tumor tissue from surrounding normal tissue intraoperatively. Subsequent pathology of this tumor tissue established it as a low grade glioma.

EXAMPLE 2

Figure 2A:
FIG. 2 illustrates identification of a malignant human CNS tumor using the methods and apparatus of the present invention.
Figure 2D:
Figure 2B:
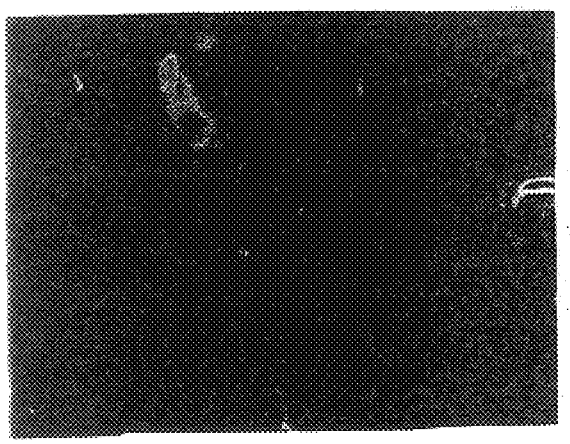
Figure 2E:
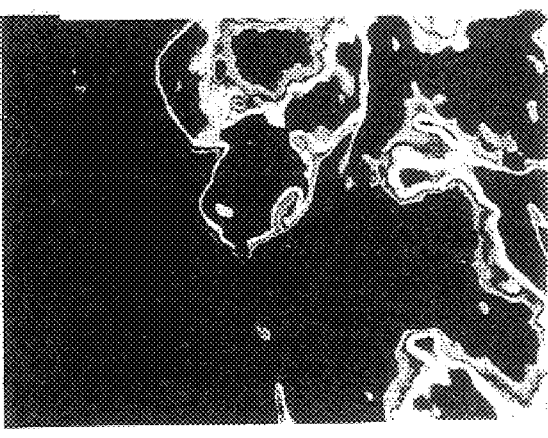
Figure 2C:
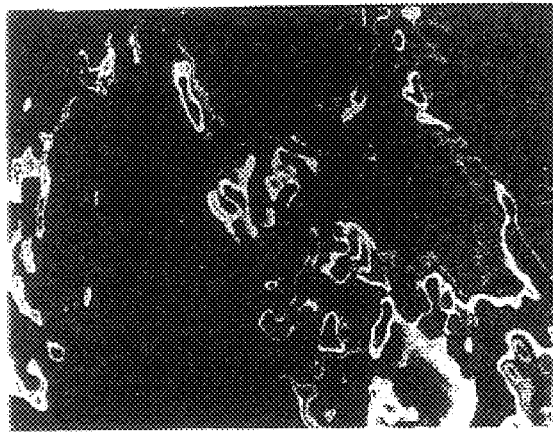

This example illustrates optical detection of a highly malignant CNS tumor (glioblastoma; astrocytoma, grade IV). FIG. 2A shows a gray-scale image in which malignant brain tumor tissue was densest in the center and to the right but that the tissue elsewhere was mostly normal. This illustrates that the optical imaging methods and apparatus of the present invention may be employed to distinguish between tumor and non-tumor tissue without the use of contrast enhancing agents, following optimization of the gain and offset on the photodetector. However, a higher resolution is obtained with the use of contrast enhancing agents. The imaging data were confirmed by pathology slides and flow cytometry data available one week after surgery. FIG. 2B is the difference image at 15 seconds after intravenous injection of indocyanine green, showing that the dynamics of dye perfusion in the first seconds in malignant tissue are similar to those in the first few seconds in benign tumor tissue. FIG. 2C shows that at 30 seconds the dye uptake in malignant tissue is even more intense by comparison to the normal tissue. FIG. 2D (1 minute after dye injection) and 2E (10 minutes after dye injection) show that dye is retained significantly longer in malignant tissue than in benign tumor tissue and, in some cases, continues to sequester in the malignant tumor tissue over longer periods of time. Therefore, using the apparatus and methods of the present invention, it is possible to identify malignant tumor tissue, distinguish intraoperatively between normal and malignant tumor tissue, and to distinguish between the various grades of tumor (e.g., normal vs. benign vs. malignant). Thus, it is possible to not only image the location and margins of tumor tissue, but also to grade the tumor with more malignant tumors retaining dye for a longer period of time than lower grade tumors.

EXAMPLE 3

Figure 3A:
FIG. 3 shows identification of small remnants of tumor tissue in the margin of a resected malignant human CNS tumor using the present invention.
Figure 3B:
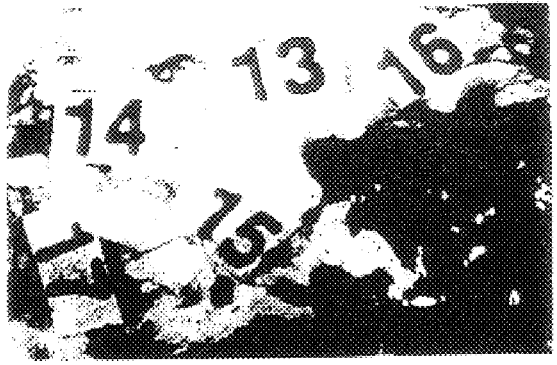
Figure 3C:
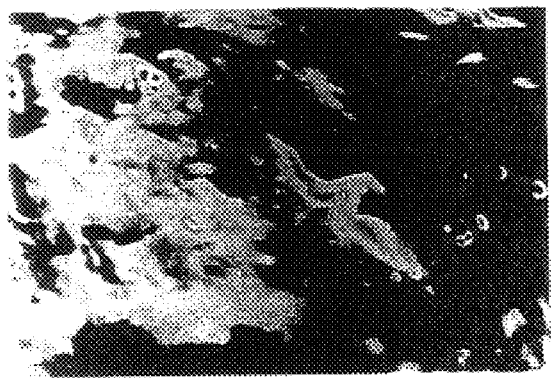
Figure 3D:
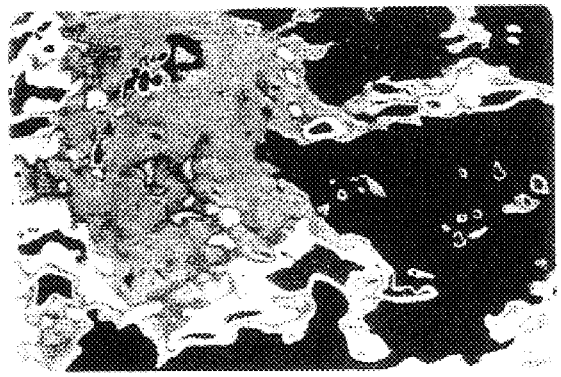

This example illustrates optical mapping of the margins of a malignant CNS tumor. FIG. 3 shows a series of images and difference images of the area of interest taken after surgical removal of the tumor and when the area was thought to be free of tumor tissue. Normally, in this size of a resection margin, only a single frozen sample would be taken for pathology analysis. For the purpose of this study, five biopsies were taken from the margin to aid in correlating the histology with the map obtained by the invention. FIG. 3A shows a gray-scale image of the tumor margin. FIG. 3B shows the margin with labels that the surgeon placed directly on the brain to identify where the surgeon was going to remove biopsy samples for histological analysis after difference images were acquired with the inventive device. FIG. 3C shows the difference image 1 minute after intravenous injection of dye and FIG. 3D shows the difference image 10 minutes after dye injection. These post-dye difference images reveal a number of sites that contain tumor tissue as well as areas of normal tissue. The accuracy of the optical imaging was confirmed post operatively by analysis of the biopsies. Note that a small area on the lower right of FIG. 3D indicates a possible region of tumor tissue that would not have been biopsied by the surgeon. These data show that the invention is able to identify small remnants of tumor tissue in a tumor margin after resection of a tumor. In addition, the invention could act as an aid to removing biopsies from the site of a tumor margin, thereby reducing the sampling error associated with the presently used random sampling technique.

EXAMPLE 4

Figure 4A:
FIG. 4 illustrates use of the methods and apparatus of the present invention to identify and characterize tumors that do not contrast enhance with MRI imaging.
Figure 4B:
Figure 4C:
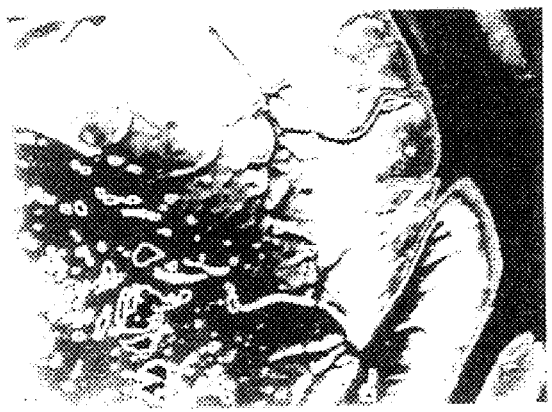
Figure 4D:

This example illustrates that the methods and apparatus of the present invention can be used to characterize and identify tumor tissue that does not contrast enhance with traditional MRI imaging. Lack of MRI enhancement is usually typical of benign tumors. However, a proportion of non-benign tumors are not observable with present MRI imaging techniques. The images in FIG. 4 are from a patient whose tumor did not contrast enhance with MRI. However, optical imaging was able to identify this tumor as a non-benign type. Pathology and flow cytometry data available one week after surgery confirmed that this tumor was an anoplastic astrocytoma. FIG. 4A shows the gray-scale image of the area of interest. FIG. 4B shows the difference image prior to dye injection. FIG. 4C shows the area of interest 1 minute after intravenous dye injection, and FIG. 4D shows the area of interest 5 minutes after dye injection. Note that the dye is retained in this tissue for a significant time. As shown in FIGS. 1, 2, and 3, this dynamic trait is a characteristic of a non-benign tumor.

EXAMPLE 5

This example illustrates a series of experiments using a rat glioma model through an intact skull to investigate whether the inventive method and inventive device could function in to image tumor tissue through an intact skull and through intact skin prior to or after surgery. Far red wavelengths of emr are known to penetrate through bone and skin. Imaging of tumor tissue was attempted through the intact skull of the rat. The extent of tumor identified was not as accurate as with the cortex exposed; however, the area lying beneath the skull with tumor tissue was easily identified and localized, and continued to concentrate dye after several minutes. Initially, after dye injection, the area of the tumor demonstrated a much larger signal than the normal brain of the contralateral hemisphere. One minute after dye injection, the dye had been cleared from the normal brain and the only residual signal remained in tumor tissue and the sagital/traverse sinuses.

Figure 5A:
FIG. 5 shows non-invasive imaging of dye dynamics and identification of glioma through the intact cranium.
Figure 5B:
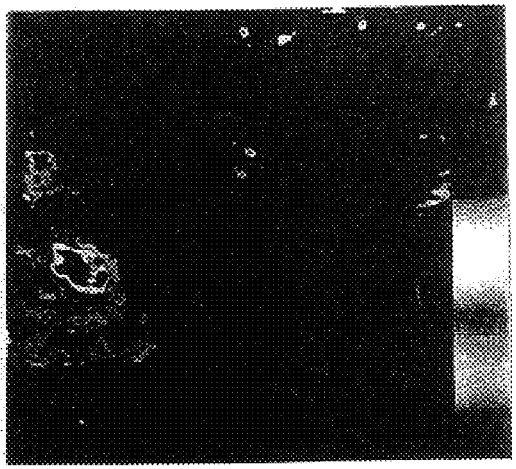
Figure 5C:
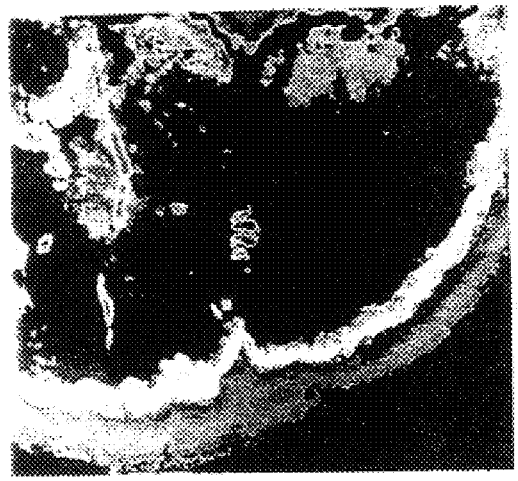
Figure 5D:
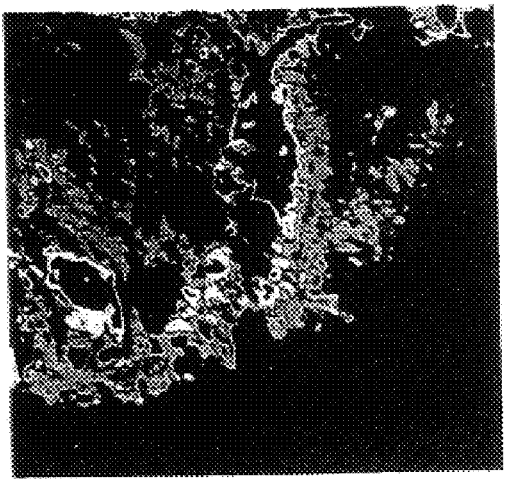

FIG. 5A is a gray scale image of the cranial surface of a rat. The sagital suture runs down the center of the image. Tumor cells had been injected into the left side some days earlier so that this animal had developed a glioma on t he left hemisphere of its brain. The right hemisphere was normal. Box 1 lays over the suspect region of brain tumor, and Box 2 lays over normal tissue. FIG. 5B is a difference image one second after indocyanine green dye had been intraveneously injected into the animal. The region containing tumor tissue becomes immediately visible through the intact cranium. FIG. 5C shows that five seconds after dye injection, the dye can be seen to profuse through both normal and tumor tissue. FIG. 5D shows that one minute after dye injection, the normal tissue has cleared the dye, but dye is still retained in the tumor region. The concentration of dye in the center of this difference image is dye circulating in the sagital sinus.

Figure 6:
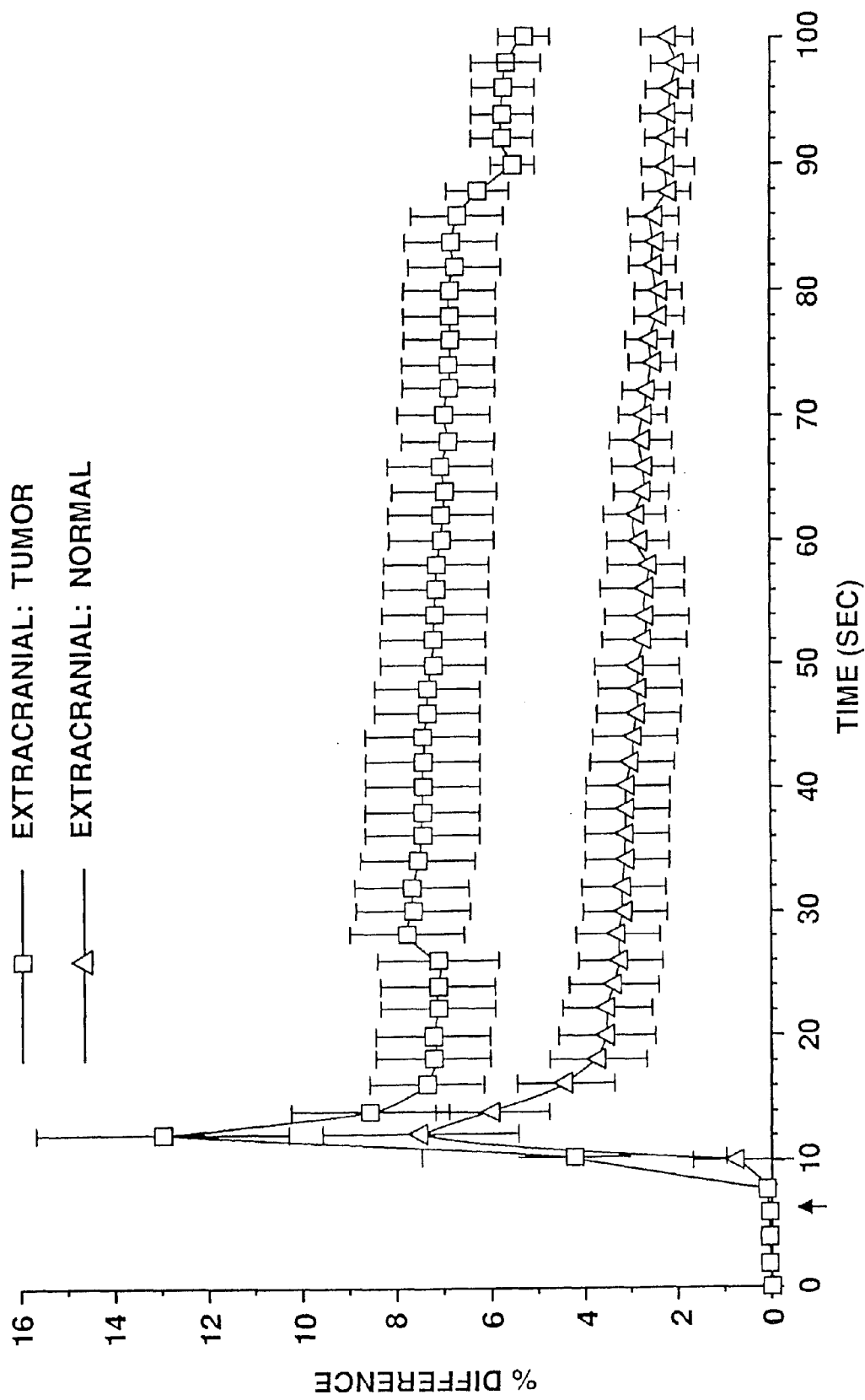
FIG. 6 illustrates the change in optical properties over time due to dye uptake and clearance in tumor vs. non-tumor tissue through the intact skull.

The time course of optical changes imaged through the cranium from ten tuns in four animals are shown in FIG. 6. The optical changes were determined by the average optical change in a box placed directly over the tumor and over the normal hemisphere. The increase in absorption is a function of the concentration of dye in the tissue at a particular time. The graph labeled "extracranial tumor" is a plot of the dynamics of the absorption changes within box 1 from FIG. 5A. The graph labeled "extracranial: normal" is a plot of the dynamics of the absorption change within box 2 from FIG. 5A. The peak optical changes for the tumor imaged through the cranium were $13.1 \pm 3.9\%$ and this was significantly greater compared to normal brain of $7.8 \pm 2.3\%$ ($p<0.01$). The plateau phase seconds after dye injection was also significantly greater in tumor tissue ($40.5 \pm 9.6\%$) compared to normal brain ($3.1 \pm 0.7\%$) ($p<0.01$).

EXAMPLE 6

This example illustrates a series of experiments using a rat glioma model intraoperatively to investigate whether the inventive methods and device could function in an operating room setting to provide real time information to a surgeon regarding resection of all tumor tissue.

The rat glioma model is a standard predictive model and was used to delineate dye uptake, clearance and overall parameters of optical imaging that result in the best images. The rat glioma model consistently produces reproducible tumors for imaging studies in which the tumor is resected under an operating microscope. A disadvantage of this model is the more sarcoma-like appearance of the tumor and a lesser degree of vascularity compared to human gliomas.

Briefly, the rat glioma model uses an ethylnitrosourea-induced F-344 rat tumor line developed from a clonal population of a spinal malignant astrocytoma. This tumor is similar to human astrocytomas microscopically and in vivo, because both have stellate-shaped cells in the brain parenchyma and both have intracytoplasmic filaments 80–100 mm in diameter as seen by scanning electron microscopy. The glioma cells were maintained in Weymouth's medium supplemented with 10% fetal calf serum. Viable cells ($5 \times 10_4$) were trypsinized from a monolayer culture and implanted stereotaxically into the right cerebral hemisphere of 30 syngeneic female rats, each weighing 140–160 g. The stereotaxic coordinates for right frontal lobe implantation were 4.5 mm anterior to the frontal zero plane, 3 mm right from the midline and 6 mm deep. The rats were anesthetized for implantation. The heads were shaved and scalps opened, and a 1 mm burr hole made at the appropriate coordinates. The cells were injected through a 27 gauge needle, the needle left in place for 30 sec post injection and the hole was covered with bone wax. The scalp was sutured and the animals observed for 3–4 hrs until they returned to normal activity and feeding. The animals were used 10–14 days after tumor implantation. In this model, animals begin to show clinical symptoms from the tumor by 16–19 days, such as decreased activity and feeding, hemiparesis and eventually succumb between 19–27 days from mass effects due to tumor expansion.

Fourteen animals underwent the complete study, including imaging before and after resection of the tumor. The animals were anesthetized with 2% isoflurane, and the femoral vein cannulated for administration of the dye. Anesthesia was maintained with a—chloralose (50 mg/kg administered ip) and urethane (160 mg/kg administered ip). The animals were placed in a stereotaxic holder. Imaging studies were then carried out before or after removal of the cranium. The tumor typically occupied the anterior one half to two thirds of the right hemisphere exposure. The compressed brain without any tumor infiltration was defined as the tumor surround to separate it from the normal hemisphere on the contralateral side.

Following imaging of the area of interest, an operating microscope was used to attempt gross total removal of the tumor. Sites were then chosen for biopsy based on optical imaging results and later analyzed histologically. The biopsy specimens were fixed in 10% paraformaldehyde, Nissl stained and mounted. All specimens were read blindly and labeled either positive or negative for tumor. These data were correlated to the optical imaging results to identify residual tumor and statistical analysis (Chi square or student t-test) was performed to determine the significance of the results.

The following imaging apparatus was employed in Examples 5 and 6. Light was from a tungsten-halogen bulb regulated by a D.C. power supply, passed through a longpass filter (690 nm), and through a right angled prism reflected through a 50 or 100 mm objective lens onto the cortical surface. The reflected light was collected by the same objective lens and focused by a projection lens onto the surface of a CCD camera (COHU 6300). The imaging apparatus was attached to the stereotaxic frame which was rigidly fixed to a vibration isolation table. Specially designed automatic warping algorithms were designed to compensate for small amounts of movement. Images (512×480 pixels) were acquired at 30 Hz and digitized at 8 bits (256 gray levels). Every 2 econds, a single image comprising 30 averaged frames was collected (1 sec) and then stored (I second).

Control images were collected prior to intravenous injection of indocyanine green dye at a dose of 1 mg/kg and then for 2 minutes after dye injection. The dye injection was made over a 1 second period while the last control image was being stored. A period of 20 minutes was allowed between dye injections to allow optical images to returnto baseline. The initial control images of each trial were subtracted from each other to insure that the baseline starting point of each trial was equivalent.

A single control image was chosen and then subtracted from each of the controls (4–6 images) and each of the post-dye injection images. The resultant image was divided by the original control image and multiplied by 100 to give a composite percentage difference for the entire sequence before and after dye injection. The optical change that occurred between separate control images were 0.2–0.7%, whereas the peak changes resulting from dye injection were in the range of 5–40%. The spatial resolution of an individual pixel in the image ranged from $13.5 \times 11.7$ mm$^2$ to $27 \times 25.4$ mm$^2$. Boxes measuring from 15–30 pixels per side were drawn on the images. The average percentage change in the individual boxes was calculated and used to demonstrate graphically the optical changes over time in the different types of tissue.

Imaging studies were performed on fourteen animals. The time course of dye perfusion through the tissue had a dynamic aspect. Optical imaging of indocyanine green dye perfusion at a dose of 1 mg/kg in 16 separate runs from a cortical surface in 9 different animals demonstrated the dynamic nature of the optical changes. In all the rat imaging examples presented herein, each image covers an area no greater than approximately 1 cm×1 cm.

FIG. 7 illustrates the dynamic differences in changes in optical property due to dye absorption between tumor and non-tumor tissue. This is the same animal as shown in FIG. 5 (see, Example 5), however the cranium has now been removed so as to expose the left hemisphere containing the glioma, and the right hemisphere containing normal tissue. FIG. 7A shows a grayscale image of the area of interest. Box 1 overlays the tumor, Box 2 overlays the tumor-surround, and Box 3 overlays normal tissue. FIG. 7B shows the difference image of the area of interest 1 second after administration of indocyanine green. During this initial time, the tumor tissue is the first to show a measurable optical change, indicating that the uptake of dye occurs first in the tumor tissue. The gray-scale bar indicates the relative magnitude of the optical changes in the sequence of difference images. FIGS. 7C and 7D show difference images of the area of interest 4 seconds and 30 seconds, respectively, after dye injection. At these intermediate stages dye appears to collect in both normal and tumor tissue. FIGS. 7E and 7F show difference images of the area of interest 1 minute and 5 minutes, respectively, after injection of dye. At these later times, it becomes clear that dye is still collecting in tumor tissue even though it is being cleared from normal tissue.

The optical signals begin to change within the first 2–3 seconds after dye injection and peak 6 seconds after injection in all three areas, tumor tissue, tumor- surround and normal brain. However, the three different tissue types are differentiated by the rate of rise over the first four seconds, the peak optical change reached, and the eventual plateau that occurs after the first 30 seconds. The tumor tissue had a significantly greater peak percentage difference change than the tumor surround which in turn had a greater peak percentage different change than the normal brain. For example, following maximization of the gain and offset on the camera controls, the peak percentage difference changes were as follows: tumor 40.5±9.6%; tumor surround 16.4±6.8%; and normal brain 9.7±4.7%.

Figure 8:
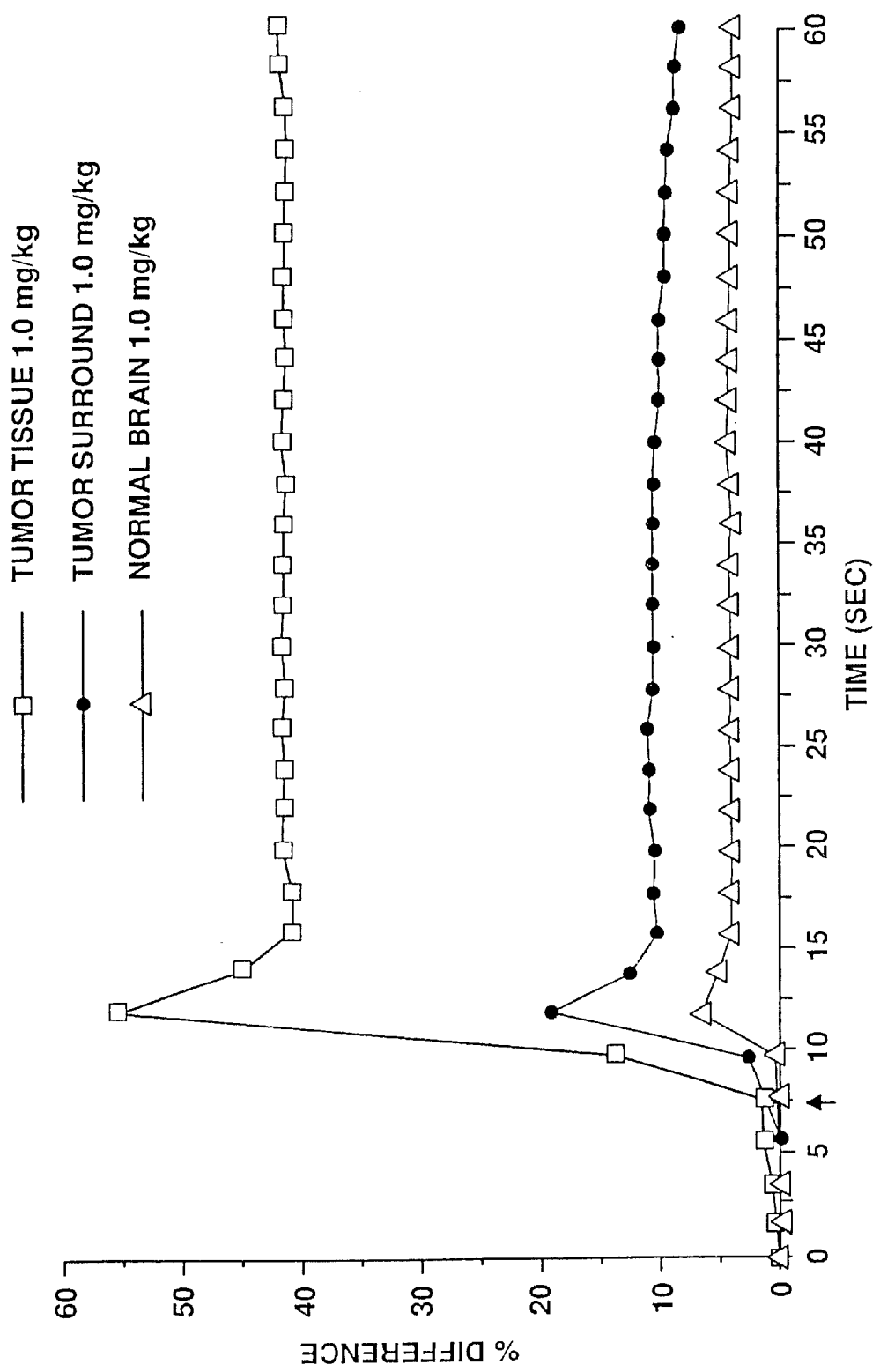
FIG. 8 shows changes in optical properties over time due to dye uptake and clearance in tumor vs. non-tumor tissue.

FIG. 8 is a plot of an average of the percentage change in optical properties over time averaged over the spatial areas indicated by boxes 1, 2, and 3 from FIG. 7A. The change in optical property is a function of the concentration of dye in the tissue at a particular time. The graphs labeled "tumor tissue," "tumor surround," and "normal brain" are plots of the change in optical properties over time within Boxes 1, 2, and 3, respectively, from FIG. 7A. These data, as well as those from FIG. 7, show that the inventive method and device is able to distinguish not only tumor from non-tumor tissue, but also tumor-surround areas which contain varying densities of tumor versus normal cells.

Since the peak optical change was always reached 4–6 seconds after dye injection, there was also a significantly faster rate of optical change in the tumor tissue compared to the tumor surround or the normal brain. A more rapid onset of dye perfusion into the tumor tissue was displayed as a faster time course. The tumor tissue had a more rapid and greater rise time than either the tumor surround or normal brain (p<0.01).

In 13 of 14 animals there was a prolonged increase (>2 min) in the optical signal in the tumor after the normal and tumor surround tissue had returned to baseline. Finally, even the normal and tumor surround tissue were significantly different in dye uptake (rise time: normal 2.4%/sec; tumor surround 4.0%/sec). Therefore, the dynamic features of dye uptake and clearance are critical for determining the type of tissue when imaging resection margins.

Figure 9A:
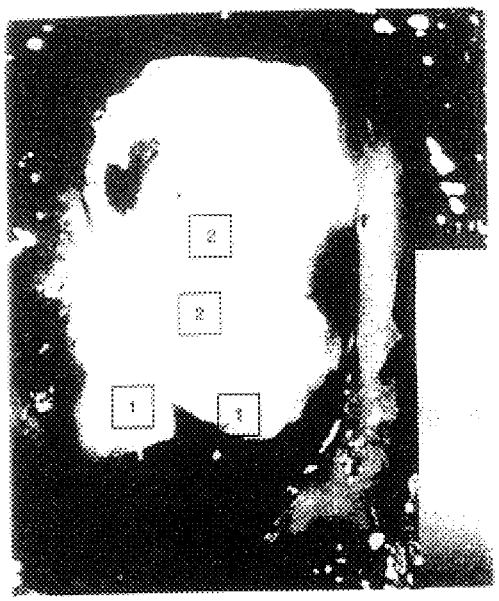
FIG. 9 demonstrates use of optical imaging of dye uptake to reveal residual traces of tumor cells in resected tumor margins. This is a continuation of the study on the same animal shown in FIGS. 5 through 8.
Figure 9B:
Figure 9C:
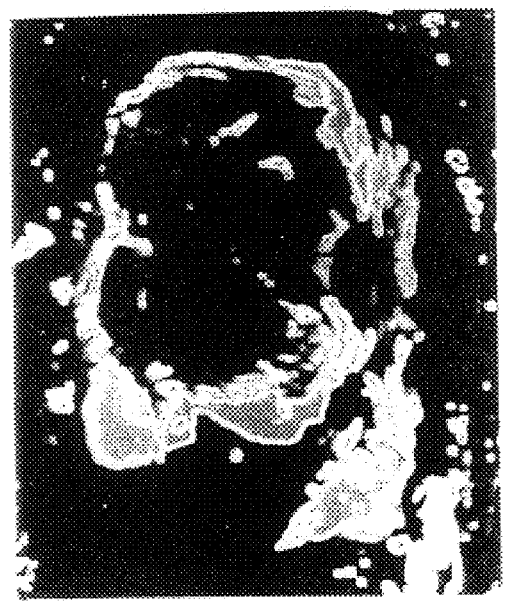
Figure 9D:

The rat glioma model also provided an opportunity to image resection margins once all visible tumor had been removed. FIG. 9A shows a higher magnification image of the left hemisphere tumor margin of the animal after the tumor had been resected. Boxes 1 overlay areas that contained small traces of residual tumor cells, and Boxes 2 overlay areas that contained only normal tissue. The grayscale bar indicates the magnitude of optical change in the difference images. FIGS. 9B, 9C, and 9D show difference images of the tumor margin 4, 30, and 60 seconds after intravenous dye injection, respectively. Minute biopsies were taken from areas that showed preferred dye containment and from areas from which the dye cleared rapidly. These biopsies were analyzed blindly and later correlated to the location from which the biopsies were taken. Those biopsies taken from areas which cleared dye were shown to contain only normal cells, whereas biopsies taken from areas which sequestered dye were shown to contain tumor cells.

The more rapid rate of rise seen in cortical surface imaging was still present for the resection margins that were positive for tumor compared to normal brain. Again, significant differences between the tumor and the normal brain existed for the rate of rise, peak optical change, and plateau 60 seconds after dye injection (all $p<0.01$). FIGS. 6–9 demonstrate that the inventive method and device can be used in combination with multiple injections of dye for repeated application throughout a tumor resection surgery (in this case, 4 separate injections of dye were given). Furthermore, extremely small islands of residual tumor can be mapped within the tumor margins.

Sensitivity and specificity of optical imaging was determined for 34 samples (n=12 animals). Of 15 biopsy sites deemed negative for tumor by optical imaging, 14 of the 15 were clear of tumor by histological analysis (sensitivity 93%). Most of the specimens that were negative for tumor were taken from the posterior wall of the tumor resection cavity or the depth of the cavity (where the hippocampus or denate gyrus were frequently biopsied). Of 19 biopsy sites deemed positive for tumor by optical imaging, 17 of the biopsy specimens were read as positive for tumor (specificity 89.5%). The two sites that were negative for tumor on histology but positive for tumor by optical imaging had increased cellularity but were deemed negative for tumor because there was no focus of tumor tissue present. The overall significance of these results are $p<0.001$.

Figure 10:
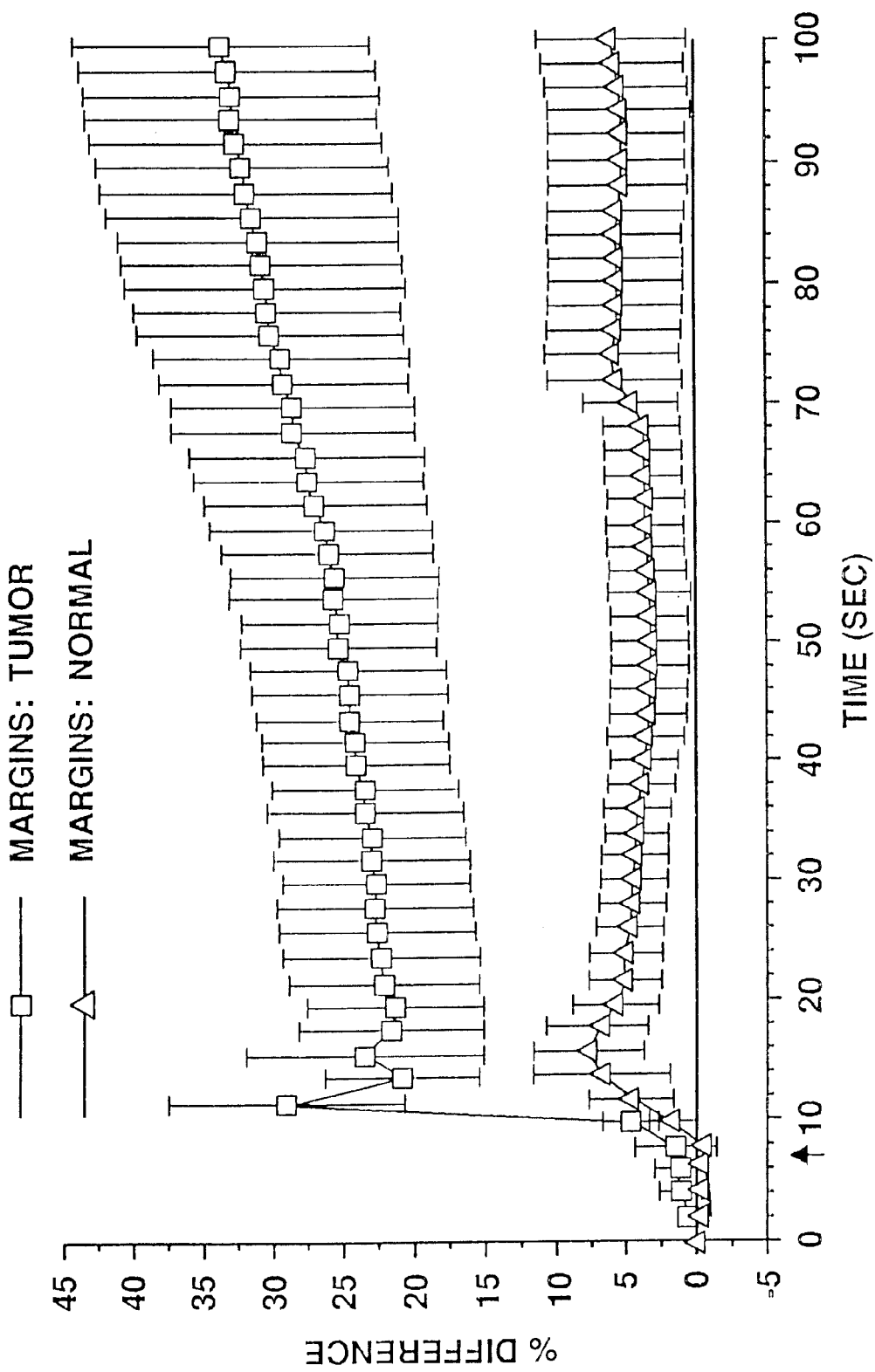
FIG. 10 shows changes in optical properties due to dye uptake and clearance in tumor vs. non-tumor tissue.

FIG. 10 shows changes in optical properties due to dye uptake and clearance in tumor vs. non-tumor tissue. Specifically, this is a plot of an average of the percentage change in optical properties over time averaged over the spatial areas indicated by Boxes 1 and 2 from FIG. 9A. The increase in absorption is a function of the concentration of dye in the tissue at a particular time. The graphs labeled "margins: tumor" and "margins: normal", are plots of the changes in optical properties over time within Boxes 1 and 2, respectively, from FIG. 9A. These data, as well as those from FIG. 9, show that the inventive device and method are able to distinguish tumor from non-tumor tissue within tumor margins with extremely high spatial and temporal resolution.

EXAMPLE 7

Sprague-Dawley rats (male and female; 25 to 35 days old) were prepared as described in Aghajanian, A. K. and Rasmussen, K., *Synapse* 31:331, 1989; and Buckmaster, P. S., Strowbridge, B. W., Schwartzdroin, P. A., *J. Neurophysiol.* 70:1281, 1993. In most hippocampal slice experiments, simultaneous extracellular field electrode recordings were obtained from CA1 and CA3 areas. For stimulation-evoked afterdischarge (13 slices, 8 animals), the concentration of $Mg^{2+}$ in the bathing medium was reduced to 0.9 mM. A bipolar tungsten stimulating electrode was placed on the Schaffer collaterals to evoke synaptically driven field responses in CA1; stimuli consisted to 100 to 300-$\mu$s-duration pulses at an intensity of four times population-spike threshold. Afterdischarges were evoked by a 2-s train of such stimuli delivered at 60 Hz. Spontaneous interictal-like bursts were observed in slices treated with the following modifications or additions to the bathing medium: 10 mM $K^+$ (6 slices; 4 animals; average, 81 bursts/min), 200 to 300 $\mu$M 4-AP (4 slices; 2 animals; average, 33 bursts/min), 50 to 100 $\mu$g M bicuculine (4 slices; 3 animals; average, 14 bursts/min), 0 mM $Mg^{2+}$ [(1 hour of perfusion) 3 slices; 2 animals; average, 20 bursts/min; (3 hours of perfusion) 2 slices, 2 animals)], 0 mM $Ca^{2+}$/6 mM KCl and 2 mM EGTA (four slices, three animals). In all treatments, perfusion with furosemide-containing medium was begun after a consistent level of bursting had been established.

For imaging of intrinsic optical signals, the tissue was illuminated with a beam of white light (tungsten filament light and lens system; Dedotec USA, Lodi, N.J.) directed through the microscope condenser. The light was controlled and regulated (power supply: Lambda Electronics, Melville, N.Y.) to minimize fluctuations and filtered (695 nm long-pass) so that the slice was transilluminated with long wavelengths (red). Image frames were acquired with a charge-coupled device camera (Dage-MTI) at 30 Hz and were digitized at 8 bits with a spatial resolution of 512 by 480 pixels by means of an Imaging Technology Series 151 imaging system; gains and offsets of the camera-control box and the analog-to-digital board were adjusted to optimize the sensitivity of the system. Imaging hardware was controlled by a 486-PC-compatible computer running software written by D. Hochman and developed with commercially available software tools (Microsoft's C/C++ Compiler and Imaging Technology's ITEX library). To increase signal-to-noise ratio, an averaged image was composed from 16 individual image-frames, integrated over 0.5 s and averaged together. An experimental series typically involved the continuous acquisition of a series of averaged images over a several minute time period; at least 10 of these averaged images were acquired as control images before stimulation. Pseudo-colored images were calculated by subtracting the first control image from subsequently acquired images and assigned a color lookup table to the pixel values. For these images, usually a linear low-pass filter was used to remove high-frequency noise and a linear-histogram stretch was used to map the pixel values over the dynamic range of the system. All operations on these images were linear so that quantitative information was preserved.

Figure 11:
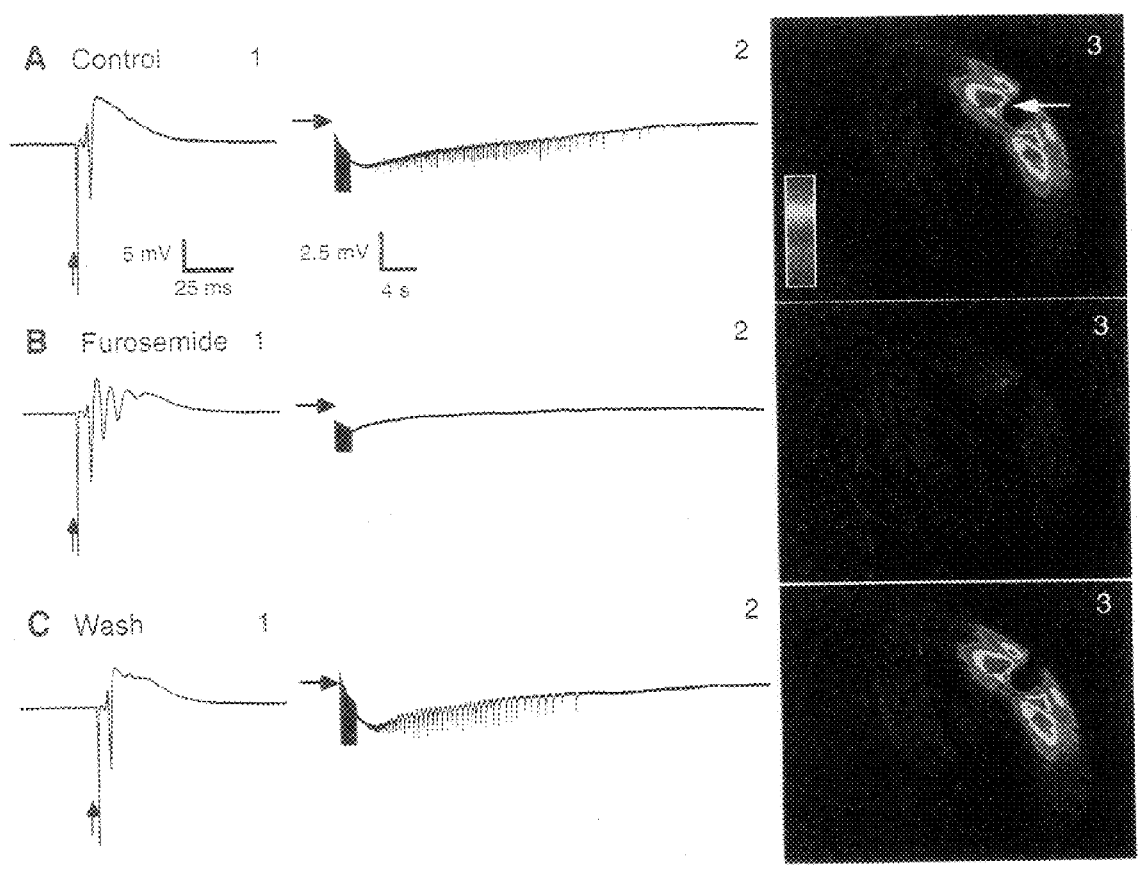

FIGS. 11A–11C show the effect of the agent furosemide on stimulation evoked afterdischarge activity in a hippocampal tissue slice comparing the field response, measurements at an extracellular electrode, and images highlighting changes in optical properties.

FIG. 11A1 illustrates that two seconds of electrical stimulation at 60 Hz elicited afterdischarge activity. FIG. 11A2 shows a typical afterdischarge episode recorded by the extracellular electrode, with the horizontal arrow indicating the baseline. FIG. 11A3 shows a map of the peak change in optical transmission through the tissue evoked by Schaffer collateral stimulation. The color bar indicates increasing magnitude of activity-evoked optical changes from the bottom to the top of the bar. The region of maximum optical change (red, yellow) corresponds to the apical and basal dendritic regions of CA1 on either side of the stimulating electrode. FIG. 11B1–11B3 illustrate responses to electrical stimulation following 20 minutes of perfusion with medium containing 2.5 mM furosemide. Both the electrical afterdischarge activity (shown in FIG. 11B2) and the stimulation-evoked optical changes (shown in FIG. 11B3) were blocked. However, there was a hyperexcitable field response (multiple population spikes) to the test pulse, as illustrated in FIG. 11B1. FIGS. 11C1–11C3 illustrate that restoration of the initial response pattern was seen following 45 minutes of perfusion with normal bathing medium.

Figures 12A, 12B, 12C, 12D, 12E:
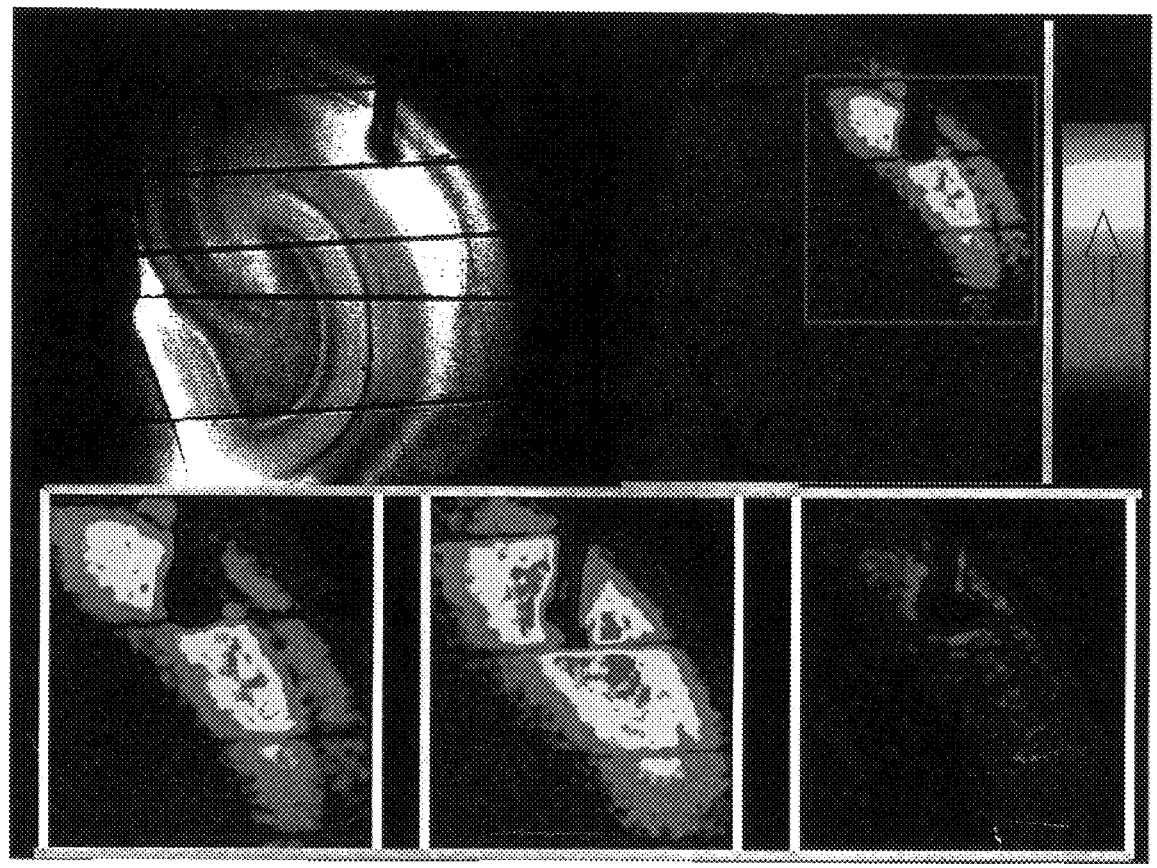
FIG. 12A illustrates an enlarged grey-scale image of an acute rat hippocampal tissue slice.
FIGS. 12B–12E illustrate enlarged, pseudo-colored images acquired as described in Example 7.

FIG. 12A illustrates an enlarged grey-scale image of an acute rat hippocampal tissue slice, observed using a CCD camera attached to a Zeiss upright microscope. FIGS. 12B–12E illustrate enlarged, pseudo-colored images acquired as described above. FIG. 12B illustrates an enlarged, pseudo-colored image acquired as described above during the peak optical change induced by electrical stimulation, with an enlarged color bar, the arrow on the color bar indicating increasing magnitude of activity-evoked optical changes. The box indicates the field of view shown magnified in FIGS. 12C, 12D and 12E. FIG. 12C illustrates the peak optical change during electrical stimulation when no epileptic activity was induced. FIG. 12D illustrates the peak optical change during electrical stimulation that resulted in epileptiform activity. A larger area of increased magnitude of changes in optical properties is observed during epileptiform activity. FIG. 12E illustrates the peak optical change during electrical stimulation following treatment with furosemide, which blocks the epileptiform activity and the intrinsic optical signal.

EXAMPLE 8

This example illustrates various methods for enhancing images obtained from tumor tissue or intrinsic signal difference images using multiple wavelength and/or laser illumination, and a method for extracting 3-D information using multiple wavelengths. We expose a region of cortex in an anesthesized rat. First, illuminating with white light from a tungsten filament lamp, we acquire a sequence of difference images prior to, during, and following electrical stimulation of this region of cortex with bipolar stimulating electrodes. Next, we acquire second and third difference image sequences, following the identical procedure as we did for the first sequence, except that in the second sequence, the cortex is illuminated with 690 nm and in the third sequence 510 nm light. The change in wavelengths is accomplished by placing 690±10 nm interference filter or a 510±10 nm interference filter between the lightsource and the brain.

We compute the contrast enhanced image by first ratioing a control 590 nm image with a control 510 nm image. Second, we ratio a 690 nm image during stimulation with the coresponding 510 nm image. We then combine the ratio images to compute the percentage difference image. In this manner, the noise has been significantly reduced; hence, the signal to noise ratio has been significantly increased.

Next, we show how to extract depth information from the multiple wavelength images that we have acquired. Longer wavelength light penetrates to a greater depth through the cortex, and shorter wavelength light to a lesser extent. Hence, the 690 nm image as penetrated cortext to x mm, and the 510 nm image to y mm, where x<y.

We subtract the 610 nm image from the 510 nm image, showing an "optical wedge" containing information from a depth of (x–y) mm to x mm within the cortical tissue. By using a series of other interference filters, we acquire a sequence of images containing information from many different depths of the cortex. It is possible to acquire 3-D information.

Next, exposing tumor tissue in a rat in which we have induced tumor growth, we repeat all of the aboe experiments showing that in a like manner, we can improve the signal to noise ratio and extract 3-D information in tumor tissue. However, instead of stimlating the tissue electrically, we inject the dyes indocyanine green of Evans blue.

Finally, we repeat the above experiments by illuminating the cortex at several different wavelengths with a dye-tunable laser (a coherent source) instead of with the non-coherent tungsten filament lamp. With the laser (or any coherent source) we have the additional advantage in that we can separate out the components of the signal due to changes in reflecting or scattering. By illuminating the cortex with the laser directly parallel to the camera (both of which are perpendicular to the brain), we are imaging reflected light only. By moving the laser at an angle θ to the camera, we are measuring changes due to scattering alone at this particular angle.

Although the present invention has been described in detail by way of description and examples for purposes of clarity of understanding, changes and modifications can be carried out without departing from the scope of the invention, which is intended to be limited only by the scope of the appended claims.

I claim:

1. A method for screening a tissue sample of a patient to spatially locate cancerous tissue in an area of interest underlying skin, tissue, bone, or dura, comprising:

positioning one or more illumination source and detector arrays in contact with the patient;

illuminating the area of interest with the illumination source array(s) emitting electromagnetic radiation (emr) having at least one wavelength which interacts with a contrast enhancing agent;

administering the contrast enhancing agent to the patient;

detecting one or more optical properties of spatially resolved areas within the area of interest with the detector array(s) subsequent to administration of the contrast enhancing agent; and comparing the optical properties of the spatially identifiable areas within the area of interest subsequent to administration of the contrast enhancing agent to either one of corresponding optical properties of different spatially resolved areas of the area of interest or a control data set representing a corresponding one or more optical properties of tissue of different spatial areas identified by type and/or condition, whereby differences in the optical properties are characteristic of normal and cancerous tissue.

2. The method of claim 1, additionally comprising transferring an acquired data set representing the optical properties of the spatially identifiable areas to a centralized data processing unit having stored therein one or more control data sets.

3. The method of claim 2, wherein the centralized data processing unit has stored therein a plurality of control data sets identified by at least one of optical property, tissue type, and normal or specified cancerous condition.

4. The method of claim 2, additionally comprising selecting a control data set from a plurality of control data sets for comparison with the acquired data set.

5. The method of claim 1, additionally comprising comparing differences in the optical properties of spatially resolved areas with statistically significant optical property difference values and producing output data identifying and spatially locating normal and cancerous tissue based on the identification of the statistically significant differences in spatially resolved areas.

6. The method of claim 1, additionally comprising comparing differences in the optical properties of spatially resolved areas and the control data set with statistically significant optical property difference values and producing output data identifying and spatially locating normal and cancerous tissue based on the identification of the statistically significant differences between the optical properties of the spatially identifiable areas and the control data set.

7. The method of claim 1, additionally comprising continuously illuminating the area of interest during detecting the optical properties of the spatially identifiable areas.

8. The method of claim 1, additionally comprising illuminating the area of interest discontinuously during detecting the optical properties of the spatially identifiable areas by modulating at least one of the frequency and the phase of the illumination.

9. The method of claim 1, additionally comprising positioning the illumination source and detector array(s) for epi-illumination of the area of interest.

10. The method of claim 1, additionally comprising positioning the illumination source and detector array(s) for transillumination of the area of interest.

11. The method of claim 1, additionally comprising administering a plurality of contrast enhancing agents and illuminating the area of interest with emr having a plurality of wavelengths that are absorbed by the plurality of contrast enhancing agents.

12. As The method of claim 1, wherein the contrast agent is selected from the group consisting of: fluorescent materials, phosphorescent materials, indocyanines, fluoresceins, hematoporphyrins, fluoresdamines, photodynamic dyes, delta 1,2 bicyclo [4,4,0] and delta.sup 1,6 bicyclo [4,4,0] functional dyes, iodine, and weak acids and bases.

13. The method of claim 1, wherein the contrast enhancing agent is linked to a targeting agent.

14. The method of claim 1, wherein the one or more optical properties are selected from the group consisting of: reflection, refraction, diffraction, absorption, scattering, birefringence, refractive index, and Kerr effect.

15. The method of claim 1, for screening a tissue sample for the presence of cancerous tissue.

16. The method of claim 1, wherein the control data set is not derived from the area of interest.

17. The method of claim 1, for screening a tissue sample selected from the group consisting of: breast tissue, uterine tissue, cervical tissue, intestinal tissue, colorectal tissue, esophageal tissue, skin, prostate tissue, lymph tissue, bone, and brain tissue.

18. The method of claim 1, comprising topically administering the contrast enhancing agent.

19. The method of claim 18, wherein the contrast agent is selected from the group consisting of: iodine and weak acids and bases.

20. The method of claim 1, comprising administering the contrast enhancing agent intravenously, subcutaneously, intraperitonally, or intraarterially.

21. The method of claim 1, wherein the control data set represents one or more optical properties of a plurality of spatially resolved areas within a control area of interest believed to contain normal tissue of the same tissue type as the area of interest.

22. The method of claim 1, comprising acquiring a plurality of data sets representing one or more optical properties of spatially resolved areas within the area of interest at preselected time intervals subsequent to administration of the contrast enhancing agent.

23. The method of claim 1, wherein the area of interest is an area of the patient believed to contain cancerous tissue, and the control data set is derived from a different area of the patient believed to contain normal tissue.

24. The method of claim 1, wherein the control data set represents one or more corresponding optical properties empirically determined to be indicative of normal tissue.

25. The method of claim 1, wherein the control data set represents one or more corresponding optical properties empirically determined to be indicative of an identified type of cancerous tissue.

26. The method of claim 1 for spatially locating cancerous tissue in an area of interest prior to removing a tissue sample.

27. The method of claim 1 for monitoring the progression or recession of cancerous tissue in the patient.

28. The method of claim 1, wherein the illuminating of the area of interest is by short pulse or pulse time illumination.

29. The method of claim 1, wherein the illuminating separates out optical properties.

30. The method of claim 1, comprising producing a comparison data set by the differences in optical properties and displaying the comparison data set as a three dimensional image.

31. The method of claim 1, comprising producing a comparison data set by the differences in optical properties at each of two or more wavelengths of emr.

32. The method of claim 1, further comprising producing a comparison data set by differences in the optical properties and processing the comparison data set to provide an enhanced contrast color image.

33. A method for in situ grading and characterizing a cancerous tissue in a patient, comprising:
   positioning one or more illumination source and detector arrays in contact with the patient;
   illuminating an area of interest lying under an exterior surface with the illumination source array(s) emitting electromagnetic radiation (emu) having at least one wavelength which interacts with a contrast enhancing agent;
   administering the contrast enhancing agent to the patient;
   detecting one or more optical properties of spatially identifiable areas within the area of interest with the detector array(s) subsequent to administration of the contrast enhancing agent; and
   comparing the optical properties of the spatially identifiable areas within the area of interest subsequent to administration of the contrast enhancing agent to either one of corresponding optical properties of different spatially resolved areas of the area of interest or a control data set representing a corresponding one or more optical properties of tissue of different spatial areas identified by type and/or condition, whereby differences in the optical properties are characteristic of cancerous tissue having different grades and characters.

34. The method of claim 1 or 33, wherein the contrast agent is selected from the group consisting of: fluorescent materials, phosphorescent materials, indocyanines, fluoresceins, fluoresdamines, delta 1,2 bicyclo and delta.sup 1,6 bicyclo functional dyes, iodine, and weak acids and bases.

35. The method of claim 1 or 33, wherein the contrast agent is a nonfluorescent material.

36. The method of claim 33, wherein the illuminating of the area of interest is by penetrating the exterior surface overlying the area of interest with the emr.

37. The method of claim 36, wherein the array of optical sources or an associated optical element contacts the exterior surface in proximity to the underlying area of interest.

38. The method of claim 36, wherein the exterior surface is skin, tissue, bone, or dura.

39. An in situ method for assessing the safety or efficacy of a treatment agent or treatment regimen for treating a cancerous condition in a patient by screening a patient tissue sample at one or more preselected times following administration of the treatment agent or treatment regimen, each screening comprising:

positioning one or more illumination source and detector arrays in contact with the patient;

illuminating an area of interest in the patient believed to contain cancerous tissue with the illumination source array(s) emitting electromagnetic radiation (emr) having at least one wavelength which interacts with a contrast enhancing agent;

administering the contrast enhancing agent to the patient;

detecting one or more optical properties of spatially identifiable areas within the area of interest with the detector array(s) subsequent to administration of the contrast enhancing agent;

comparing the optical properties of the spatially identifiable areas within the area of interest subsequent to administration of the contrast enhancing agent to either one of different spatially resolved areas of the area of interest or a control data set representing a corresponding one or more optical properties of tissue identified by type and/or condition, whereby differences in the optical properties are characteristic of normal and cancerous tissue; and determining whether the treatment agent or treatment regimen is safe or effective.

40. A system for in situ detection of tissue having optical properties different from the optical properties of surrounding tissue in a patient, comprising:

array of optical sources for illuminating an area of interest with electromagnetic radiation (emr) having at least one wavelength of from 450 nm to 2500 nm;

an array of optical detectors for detecting and acquiring a data set representing one or more optical properties of spatially resolved areas within the area of interest;

a central data processing unit in communication with the optical source and the optical detector for receiving the data set from the optical detector(s), comparing the optical properties of spatially identifiable areas within the area of interest to either one of different spatially resolved areas of the area of interest or a control data set representing one or more corresponding optical properties of tissue identified by type and/or condition, and producing output data identifying differences in the optical properties of spatially resolved areas within the acquired data set, or identifying differences in the optical properties of the acquired data set and the control data set; and a display unit for displaying the output data.

41. An optical system according to claim 40, wherein the central data processing unit has stored therein a plurality of control data sets, each of the control data sets being identified by at least one of tissue type and tissue condition.

42. An optical system according to claim 40, for in situ detection and spatial localization of normal and abnormal tissue in a patient.

43. An optical system according to claim 40, wherein the optical detectors are selected from at least one of photodiodes, photo multiplier tubes, photon intensifiers, cameras, video cameras, photon sensitive semiconductor devices, and CCD cameras.

44. An optical system according to claim 40, additionally comprising at least one fiber optic strand in communication with at least one optical source.

45. An optical system according to claim 40, wherein the optical sources and detectors are mounted on an invasive or semi-invasive instrument.

46. An optical system according to claim 40, wherein the optical sources and detectors are mounted on a biopsy instrument.

47. An optical system according to claim 40, wherein the data set acquired by the optical detector(s) is analog and the data set is converted to a digital form prior to comparing differences in the optical properties in the central data processing unit.

48. An optical system according to claim 40, wherein the optical sources provide continuous illumination during data acquisition.

49. An optical system according to claim 40, wherein the optical sources provide non-continuous illumination during data acquisition.

50. An optical system according to claim 40, wherein the optical sources provide non-continuous illumination by modulating at least one of the frequency and the phase of the illumination during data acquisition.

51. An optical system according to claim 40, wherein the output data is in the form of a graph.

52. An optical system according to claim 40, wherein the output data is in the form of an image.

53. An optical system according to claim 40, comprising at least one fiber optic stand in communication with at least one optical detector.

54. A method for screening a tissue sample of a patient to spatially locate cancerous tissue in an area of interest underlying skin, tissue, bone, or dura, comprising:

positioning one or more illumination source and detector arrays in contact with the patient;

illuminating the area of interest with the illumination source array emitting electromagnetic radiation (emr) having at least two different wavelengths which interact with a contrast enhancing agent;

administering the contrast enhancing agent to the patient;

detecting one or more optical properties of spatially resolved areas within the area of interest for each wavelength with the detector arrays subsequent to administration of the contrast enhancing agent; and comparing the optical properties of the spatially identifiable areas within the area of interest subsequent to administration of the contrast enhancing agent to a control data set representing one or more optical properties of the area of interest corresponding to each wavelength, whereby differences in the optical properties are characteristic of normal and cancerous tissue.

55. The method of claim 54, wherein by the comparing, a first comparison set and second comparison set are obtained for each wavelength and further comprising obtaining an enhanced comparison data set by ratioing a first comparison set to a second comparison set.

56. The method of claim 54, wherein three-dimensional information is obtained of the area of interest.

* * * * *